United States Patent
Nan et al.

(10) Patent No.: US 8,455,510 B2
(45) Date of Patent: Jun. 4, 2013

(54) RAPAMYCIN CARBONIC ESTER ANALOGUES, PHARMACEUTICAL COMPOSITIONS, PREPARATIONS AND USES THEREOF

(75) Inventors: Fajun Nan, Shanghai (CN); Jian Ding, Shanghai (CN); Jianping Zuo, Shanghai (CN); Linqian Yu, Shanghai (CN); Linghua Meng, Shanghai (CN); Yangming Zhang, Shanghai (CN); Na Yang, Shanghai (CN); Min Gu, Shanghai (CN)

(73) Assignee: Shanghai Institute of Materia Medica, Chinese Academy of Sciences, Shanghai (CN)

( * ) Notice: Subject to any disclaimer, the term of this patent is extended or adjusted under 35 U.S.C. 154(b) by 0 days.

(21) Appl. No.: 13/119,700

(22) PCT Filed: Sep. 17, 2009

(86) PCT No.: PCT/CN2009/001042
§ 371 (c)(1), (2), (4) Date: Mar. 17, 2011

(87) PCT Pub. No.: WO2010/031251
PCT Pub. Date: Mar. 25, 2010

(65) Prior Publication Data
US 2011/0166172 A1    Jul. 7, 2011

(30) Foreign Application Priority Data
Sep. 18, 2008    (CN) .......................... 2008 1 0200073

(51) Int. Cl.
C07D 498/18 (2006.01)
A61K 31/436 (2006.01)
A61P 35/00 (2006.01)

(52) U.S. Cl.
USPC .......................... 514/291; 540/456

(58) Field of Classification Search
USPC .......................... 540/456; 514/291
See application file for complete search history.

(56) References Cited

U.S. PATENT DOCUMENTS
6,277,983 B1    8/2001  Shaw et al.
2009/0253733 A1 * 10/2009  Rhodes et al. ................ 514/291

FOREIGN PATENT DOCUMENTS
EP    0 669 923 A1    5/1994
WO    94/25022 A1    11/1994
WO    95/28406 A1    10/1995

* cited by examiner

*Primary Examiner* — Bruck Kifle
(74) *Attorney, Agent, or Firm* — Baker & Hostetler LLP

(57) ABSTRACT

Rapalogs of formula I, pharmaceutically acceptable salts, pharmaceutical compositions, and preparation methods and uses thereof. The rapalogs have the structure of formula I and can be used as an anti-tumor medicament. Comparing with rapamycin, the rapalogs of the present invention exhibit enhanced water solubility, and improved pharmacological and pharmacokinetic properties by introducing a hydrophilic and polar group such as a hydroxyl.

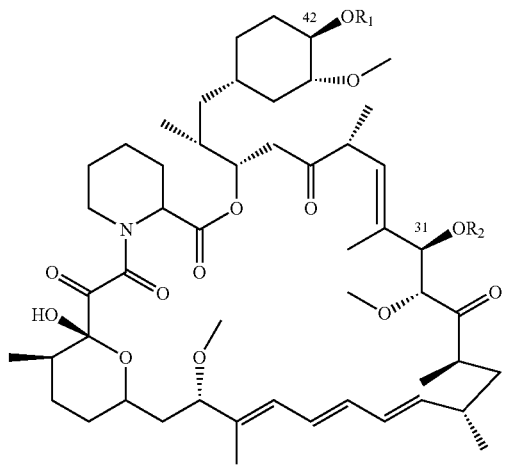

8 Claims, 12 Drawing Sheets

RAPAMYCIN CARBONIC ESTER ANALOGUES, PHARMACEUTICAL COMPOSITIONS, PREPARATIONS AND USES THEREOF

TECHNICAL FIELD

The present invention relates to pharmaceutical chemistry, more particularly, to a series of rapamycin analogs (rapalogs) having a novel structure, pharmaceutically acceptable salts thereof and pharmaceutical compositions comprising the same, and also to the preparation methods thereof, and their use in preparing anti-tumor and/or anti-cancer medicaments or immunodepressants.

BACKGROUND ART

Cancer, which are a series of diseases characterized in abnormal cell proliferation and metastasis, has been one of the serious diseases that threaten the human health. According to the statistics from WTO, about 6 million peoples suffer newly from cancer every year all over the world. In China, cancer has been the second largest cause of death after cardio-cerebrovascular diseases.

At present, the common anti-tumor medicaments used in clinic are cytotoxic drugs, which have disadvantages such as poor selectivity, serious adverse reactions, and being easy to develop resistance. As the rapid development of techniques relating to biological genetic engineering and of research on molecular oncology and molecular pharmacology, it is gradually comprehended that the substantial mechanism of cells' cancerization involves the incoordinate cell signaling, i.e., the over-active signal transduction results in celluar immortalization as to most kinds of tumors. Therefore, molecules involved in the cell signaling are the important key to find novel anti-tumor medicaments, that is to say, the target sites of the key enzyme of the signal transduction pathway relating to tumor cell differentiation and proliferation can be used as the screening sites to find out a new anti-tumor medicament both exhibiting high performance, specificity and low toxicity and specifically combining with those target sites. At present, the said screening method has become a new way to investigate and develop anti-tumor medicaments.

PI3K-mTOR signal transduction pathway is one of the major protein tyrosine kinase signal transduction pathways. Phosphatidylinositol 3 kinase (PI3K) activates protein kinase B(PKB) by phosphorylation, and then the latter activates the mammalian target of rapamycin (mTOR) by phosphorylation. mTOR directly or indirectly participates in a plurality of regulations relating to cell proliferation and growth, and therefore is considered as a central regulator of cell proliferation. Many findings of research show that PI3K-mTOR signal transduction pathway is abnormally expressed in tumor cells, and plays an important role in the generation and development of a tumor. Therefore, PI3K-mTOR signal transduction pathway has become a promising target sites as to tumor therapy, because it is possible to specifically inhibit the growth of tumor cells if the said pathway is blocked, especially the activity of mTOR is inhibited.

Rapamycin, also called sirolimus, is a triene macrolide antibiotic first obtained through fermentation from the bacterium *Streptomyces hygroscopicus* isolated on the island of Rapa Nui by Wyeth Ayerst lab in 1975. It has antibacterial activities, and has been applied in clinic as a potent immunodepressant. Recent researches have shown that rapamycin exhibits significant antineoplasmic activities as a specific inhibitor for mTOR. In vitro, the growth of rhabdomyosarcoma cells can be significantly inhibited by only 1 ng/ml of rapamycin. Results obtained from many labs all over the world have also verified that rapamycin is a very good candidate for anti-tumor therapy. Rapamycin exhibits strong inhibitory effects on many tumors, such as rhabdomyosarcoma, neuroblastoma, spongioblastoma, medulloblastoma and small cell lung cancer, etc., and it has been clearly verified that its inhibitory effects on the growth of tumor cells are due to the combination with mTOR. Although rapamycin has exhibited fairly well anti-tumor activities before clinical application, its low water-solubility and chemical stability due to the macrolide structure thereof restrict its clinical development.

Recently, various rapalogs for mTOR-target therapy of tumor have been developed by many pharmaceutical companies. Among them, the representatives are CCI-779 (TemRapamycin) from Wyeth Co., RAD-001 (Everolimus) from Novarti Co. and AP23576 from Ariad Co. These rapalogs show similar anti-tumor effects as those of rapamycin and improved pharmacological properties without apparent adverse reactions. CCI-779 is suitable for intravenous injection and has been applied for the clinical therapy of patients suffered from advanced renal cancer. RAD-001 is suitable for oral administration and has been used in clinical tests at α stage for the treatment of small cell lung cancer. AP23576 has been used in clinical tests at β stage for the treatment of hematological cancers or solid tumors, showing a good prospect of being used as a drug. Therefore, it is desired to find an anti-tumor medicament with a superior activity, low toxicity and high specificity by structural modification using rapamycin as the mother core, which is much valuable in application.

DISCLOSURE OF THE INVENTION

The present invention provides a series of rapalogs with novel structures by modifying and reconstituting the hydroxyl groups at 31-position and 42-position of rapamycin, which have in vitro and in vivo anti-tumor and/or anti-cancer activities or immunosuppressive activities. After evaluated with respect to water-solubility, in vitro and in vivo pharmacodynamic effects, oral bioavailability and drug metabolism, the said compounds deserve further investigation to be used in the preparation of an anti-tumor medicament or as a candidate for immunodepressant.

Therefore, one object of the present invention is to provide a series of rapalogs having novel structures or the pharmaceutically acceptable salts thereof.

Another object of the present invention is to provide a pharmaceutical composition having the said rapalogs or the pharmaceutically acceptable salts thereof as an active component.

A further object of the present invention is to provide a use of the said rapalogs or the pharmaceutically acceptable salts thereof in preparing anti-tumor and/or anti-cancer medicaments or immunodepressants.

The rapalogs provided by the present invention has the structure of formula I:

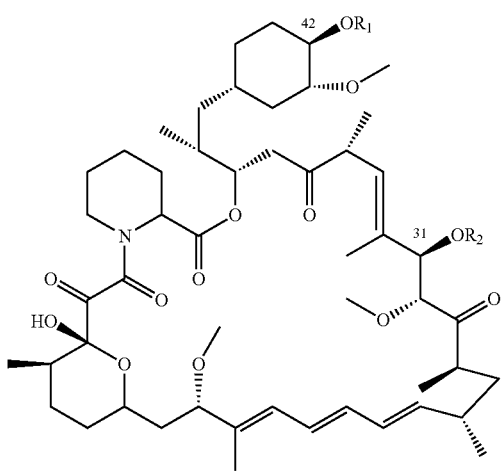

wherein,
R₁ and R₂ are each independently H or

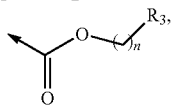

wherein, n is an integer of 1 to 6, R₃ is

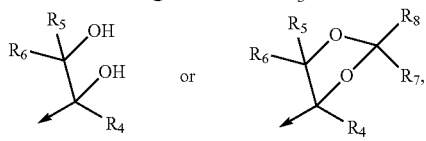

wherein, R₄, R₅ and R₆ are each independently H, C1-C6 hydroxyalkyl, C1-C6 alkyl or C2-C6 alkenyl, and R₇ and R₈ are each independently H or C1-C6 alkyl, and R₁ and R₂ can not be H at the same time.

In a preferable embodiment of the present invention, the R₁ and R₂ are each independently H or

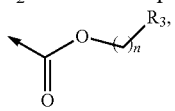

wherein, n is an integer of 1 to 4, R₃ is

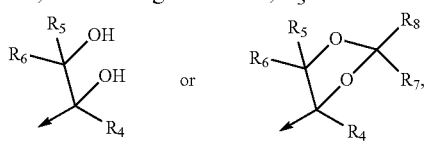

R₄, R₅ and R₆ are each independently H or C1-C4 hydroxyalkyl, and R₇ and R₈ are each independently C1-C4 alkyl, and R₁ and R₂ can not be H at the same time.

In a further preferable embodiment of the present invention, the R₁ and R₂ are each independently H or

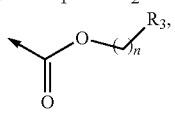

wherein, n is an integer of 1 to 2, R₃ preferably is

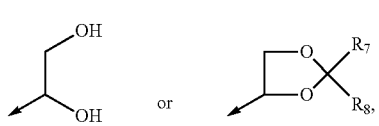

and R₇ and R₈ preferably are C1-C4 alkyl, and R₁ and R₂ can not be H at the same time.

Still further, the representative compound of the present invention is one selected from the group consisting of

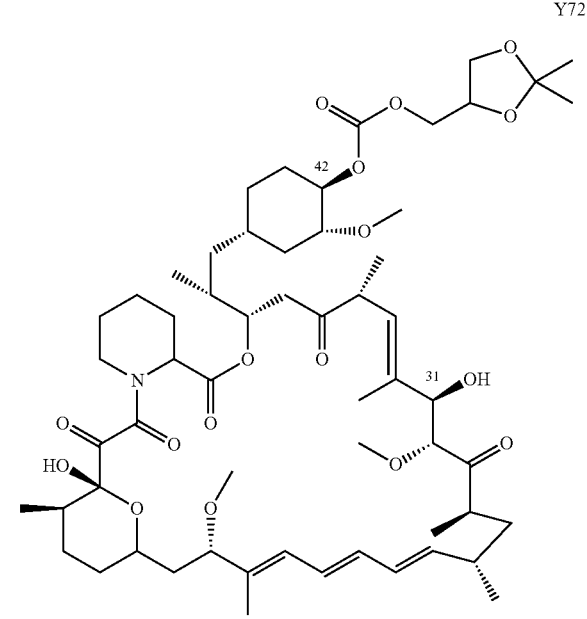

Y72

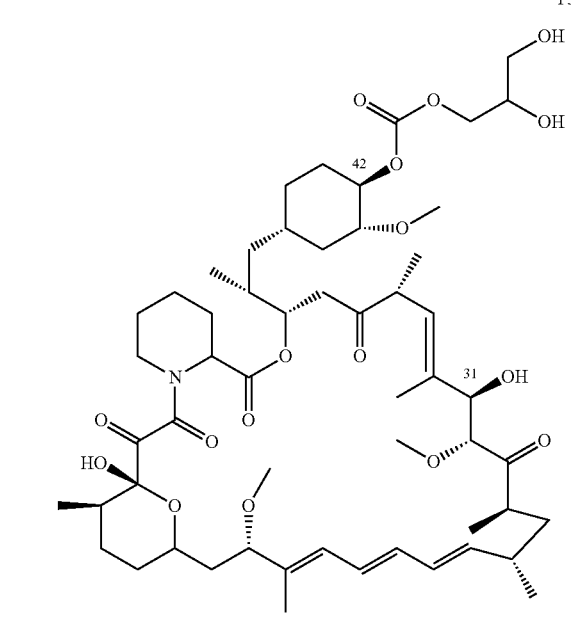

Y31

Y230

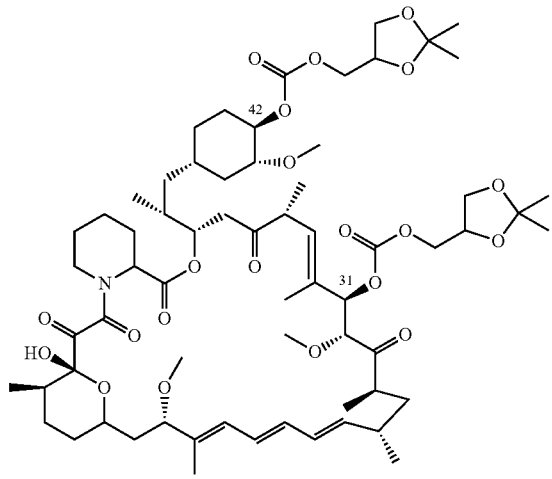

Y50

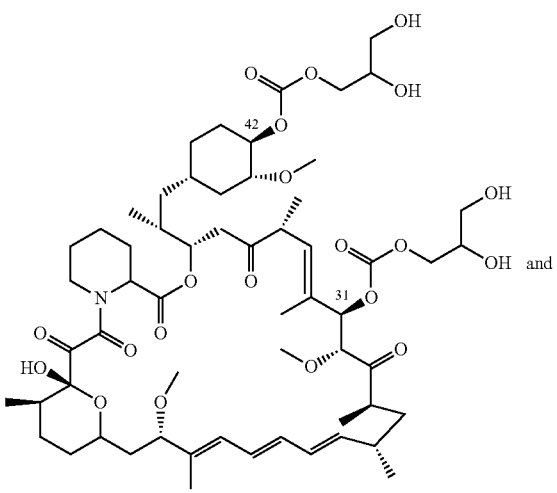  and

Y31-1

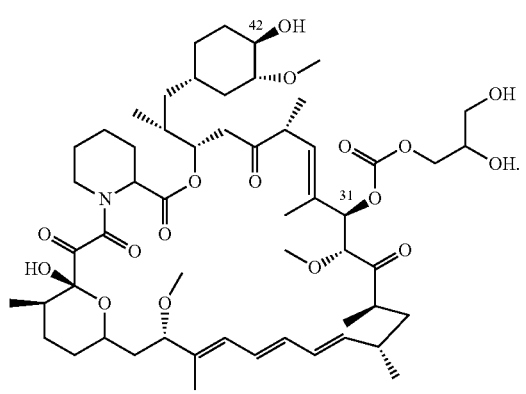

The rapalogs or the pharmaceutically acceptable salts thereof according to the present invention may be various optical isomers or a mixture thereof, when $R_3$ comprises a chiral site.

The present invention provides a method for preparing the rapalogs of formula I, in case of when both $R_1$ and $R_2$ are the same

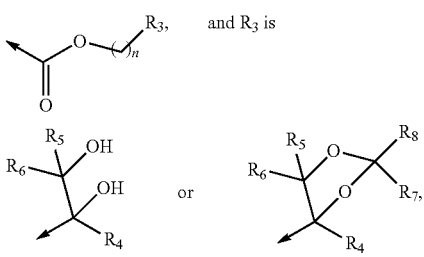

the rapalogs is prepared according to following process:

an alcohol of formula 1 reacts with a carbonyl compound $R_7COR_8$ or a diol-carbonyl condensation compound thereof (such as acetone, and 2,2-dimethoxypropane et al.) in a solvent such as DMSO, DMF and the like under the catalytic action of p-toluene sulfonic acid to produce an alcohol of formula 2; triphosgene reacts with the alcohol of formula 2 in the presence of a base to produce an acyl chloride 3; and the acyl chloride 3 then reacts with rapamycin in the presence of a base to produce a 31,42-disubstituted rapalogs wherein $R_3$ is

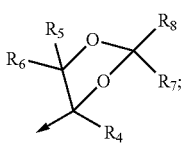

the resultant rapalogs is further hydrolyzed into a rapalogs wherein, $R_3$ is

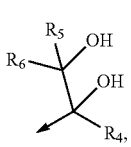

as illustrated in the following scheme:

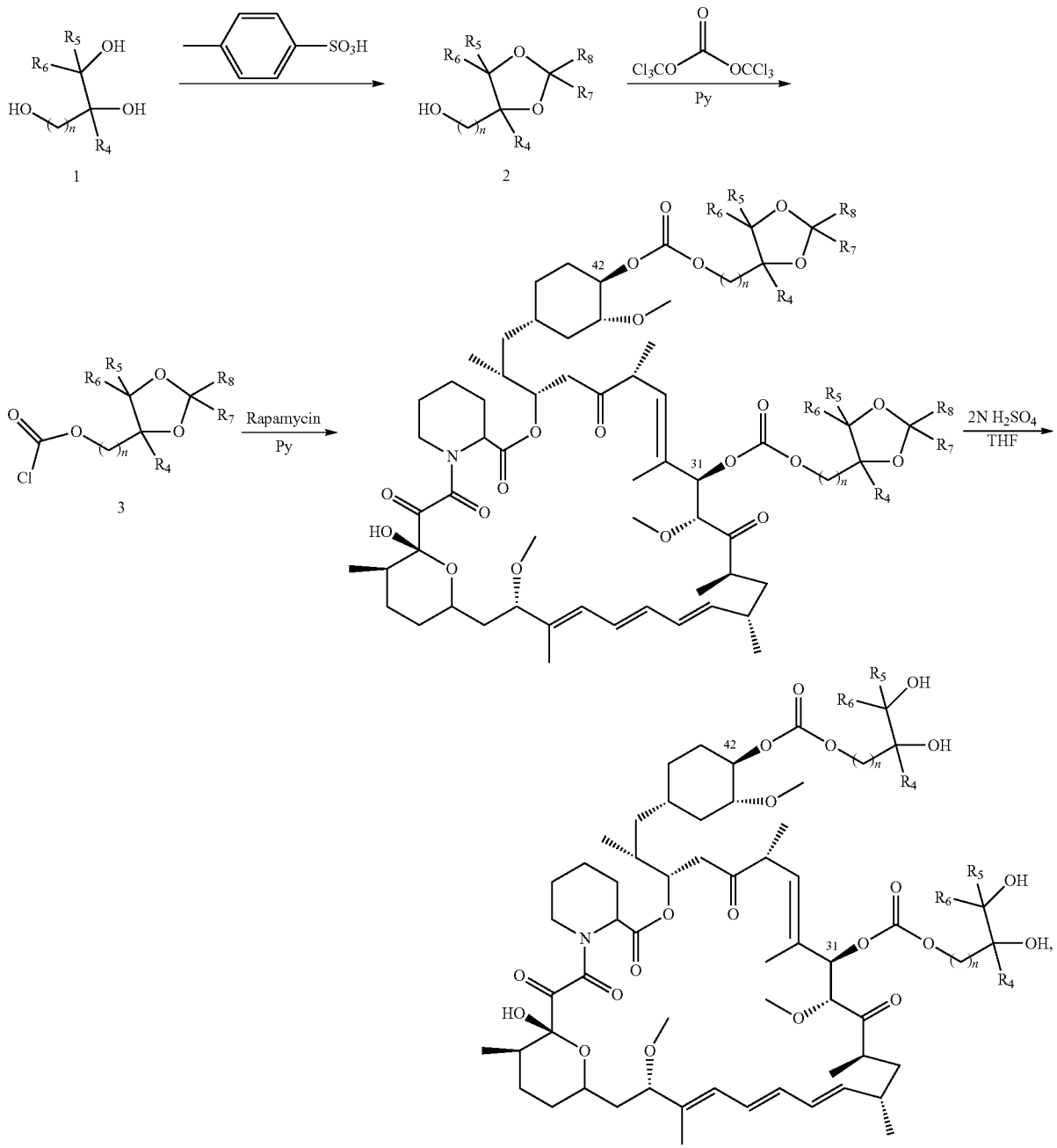

wherein, compound 1 is commercially available, for example, from Sinopharm Chemical Reagent Co. Ltd, Adlrich Co. and the like.

More particularly, the two adjacent hydroxy groups of alcohol 1 are protected to obtain an alcohol 2. In a solvent selected from DMA, DMF, acetonitrile, dichloromethane and tetrahydrofuran, the alcohol 2 reacts with triphosgene in the presence of a basic compound such as pyridine, triethylamine and diethylpropylethylamine and the like to produce an acyl chloride 3. Then, in a solvent selected from DMA, DMF, acetonitrile, dichloromethane and tetrahydrofuran, rapamycin reacts with the acyl chloride 3 to produce a 31,42-esterified rapalogs in the presence of a basic compound such as pyridine, triethylamine, DMAP, diethylpropylethylamine and the like, wherein, the rapamycin was purchased from Fujian Kerui Parmaceutical Co. Ltd.

In addition, when $R_1$ and $R_2$ are different and are respectively H or

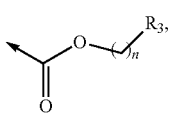

wherein $R_3$ is

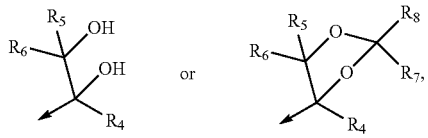

the rapalogs of the present invention may be synthesized by selective protection of the 31- and 42-hydroxyl groups of rapacimin to obtain a monosubstituted rapalogs or a disubstituted rapalogs with different substituents. Because there are two secondary alcohol groups at the 31- and 42-positions of rapamycin, it was difficult to achieve the selective mono-esterification at the 42- or 31-position of rapamycin. Although, U.S. Pat. No. 6,277,983 disclosed a method for preparing a 42-monoesterified compound, it has a poor operability and need a longtime low temperature condition. During repeating the method disclosed by U.S. Pat. No. 6,277,983, the present inventor found that rapamycin rapidly converted into a 31,42-disubstituted product during the reaction. The present inventor also found that as time passed by, the above disubstituted product would be further converted into a 31-monosubstituted product of rapamycin and some rapamycin. Therefore, a 31-monosubstituted product of rapamycin may be prepared by controlling the reaction time through tracing the reaction by TLC.

By using an appreciate proportion of imidazole and trimethyl chlorosilane with a solvent selected from dichloromethane, dichloroethane, ethyl acetate, tetrahydrofuran, acetonitrile and DMF, rapamycin can be rapidly and effectively converted at room temperature into a 31-monosubstituted product, rapamycin-31-OTMS. Thereafter, a 42-monoprotected product, rapamycin-42-OTBS may be obtained through a process of TBS-protecting 42-hydroxyl of the rapamycin-31-OTMS and then deprotecting the unstable protective silicon group.

The reaction scheme is as follows:

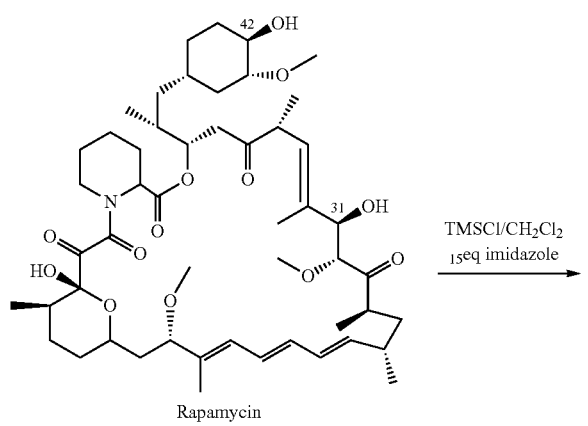

Rapamycin

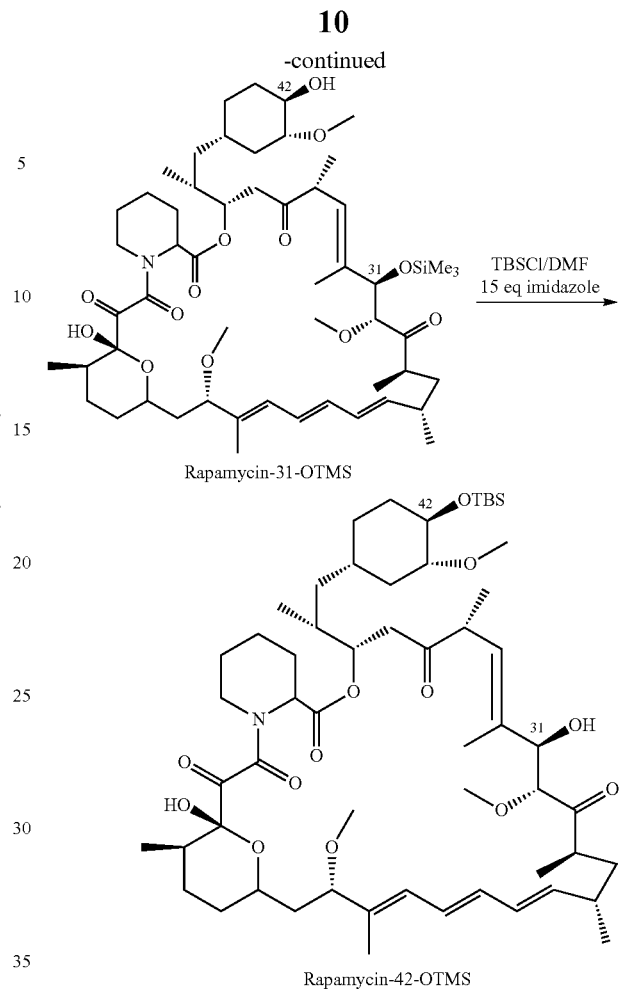

Rapamycin-31-OTMS

Rapamycin-42-OTMS

Wherein, in the preparation of rapamycin-31-OTMS, the reaction solvent may be one selected from dichloromethane, dichloroethane, ethyl acetate, tetrahydrofuran, acetonitrile and N,N-dimethylformamide, the reaction temperature may be in the range of 0° C. to 40° C., the reaction time may be in the range of 2 hours to 48 hours, and the equivalent ratio of rapamycin:imidazole:trimethyl chlorosilane may suitably be 1:5-30:2-6, and most preferably, 1:10-15:2-4.

Then, rapamycin-31-OTMS may directly react with the acyl chloride 3

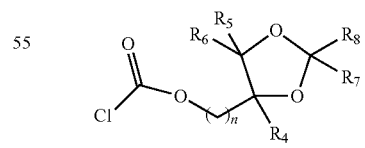

3 to produce a 42-esterified product, which is deprotected the 31-protecting group to obtain a corresponding 42-monoesterified rapalogs.

The 42-monoesterified product rapamycin-42-OTBS may react with the acyl chloride 3

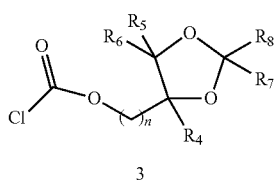

3 to produce a 31-esterified product, which is deprotected the 42-protecting group to obtain a corresponding 31-monoesterified rapalogs.

The pharmaceutically acceptable salts of rapalogs according to the present invention may be prepared by conventional methods from the rapalogs of the present invention.

The pharmaceutical composition according to the present invention may contain a therapeutically effective amount of one or more rapalogs or pharmaceutically acceptable salts thereof of the present invention as an active component, and one or more pharmaceutically acceptable carriers.

In addition, through experiments, it was found that the rapalogs or pharmaceutically acceptable salts thereof of the present invention exhibit substantially superior anti-tumor and anti-cancer activities to rapamycin, with good pharmacological and pharmacokinetic properties, and thus can be used in preparing medicaments for treating human rhabdomyosarcoma, prostate cancer, non-small-cell lung cancer, breast cancer, colon cancer, renal cancer, adenocarcinoma of lung, uterine cervix cancer or leucocythemia. Further, the rapalogs or pharmaceutically acceptable salts thereof of the present invention show improved water solubility while maintaining an immunosuppressive activity comparable to or superior to that of rapamycin.

Then anti-tumor compounds provided by the present invention are effective against various tumor cells or cancer cells, and have enhanced water solubility and improved pharmacological properties by introducing hydrophilic and polar groups such as hydroxyl, when compared with rapamycin. In vitro experiments on various tumor cell lines demonstrate that the compounds of the present invention have remarkably superior anti-tumor activities to rapamycin (as shown in tables 1 to 5 and FIGS. 3 to 9). The studies on cell level indicate that Y50 exhibits inhibitory activities against the growth of tumor cells, such as Rh30, PC-3, MCF-7 and CAKI-1 and HL-60, which are comparable with rapamycin (as shown in FIG. 1), and can concentration-dependently inhibit the catalytic ability of mTOR for the phosphorylation of the downstream substrates thereof in Rh30, PC-3, MCF-7 and CAKI-1 cells, wherein it has an inhibiting ability comparable to rapamycin at the same concentration (as shown in FIG. 2). As shown in table 1 and FIG. 9, SPR (surface plasma resonance) results suggest that 1) all of rapamycin, CCI-779, Y50 and Y31 can concentration-dependently bind to FKBP12, and when compared with Rapamycin at the same concentration, Y50 and Y31 have a higher response unit (RU) than rapamycin, indicating that Y50 and Y31 have a stronger binding with FKBP-12 than rapamycin at the same concentration; 2) the concentration of Y50 and Y31 to reach the saturated binding with FKBP12 is lower than that of rapamycin; 3) Y50 and Y31 have a lower dissociation rate with FKBP12 than rapamycin and CCI-779. The dissociation constants of Y50 and Y31 are lower than those of rapamycin and CCI-779. Animal experiments reveal that orally administered Y50 exhibits remarkably superior inhibitory effects against the growth of RH-30 human rhabdomyosarcoma xenograft on nude mice (as shown in table 2 and FIGS. 3 to 4). Orally administered Y50 also exhibits remarkably superior inhibitory effects to rapamycin against the growth of PC-3 human prostate xenograft on nude mice (as shown in table 3 and FIGS. 5 to 6). The T/C values of Y50 are 10.0% and 40.2% respectively, and the corresponding T/C values of rapamycin (positive control) under the same dosages are 30.9% and 46.5% respectively. Orally administered Y31 further exhibits remarkable inhibitory effects against the growth of U2SO human osteosarcoma xenograft on nude mice. In the group of low dosage (2.5 mg/kg), CCI-779 and rapamycin do not have apparent inhibitory effects against U2SO human osteosarcoma xenograft on nude mice with T/C values of 69.0% and 60.0% respectively, while compound Y31 under the low dosage (2.5 mg/kg) exhibits remarkably superior inhibitory effects against the growth of the xenograft to rapamycin and CCI-779 (as shown in table 5 and FIG. 8).

Further experiments of the compounds provided by the present invention on their anti-tumor abilities show that when compared with rapamycin and marketed rapamycin analogues CCI-779, Y31 exhibits superior pharmacokinetic parameters (as shown in tables 6 to 9 and FIGS. 10 to 12), which may be due to the introduction of the hydrophilic and polar groups such as a hydroxyl. Particularly, it should be pointed out that Y31 in a tumor tissue after administration has the best selective absorption among all the tested compounds (as shown in table 9 and FIG. 12). It has been found from the experiments that after administered to nude mice, Y31 rapidly converts into its metabolite rapamycin, and the prototype drug in plasma and tissue has a low concentration with a highest concentration of less than 20 ng/ml or ng/g, and 5 h after administration, the prototype drug is not detectable. After administration, the ratios of rapamycin exposure in plasma, liver and tumor tissues between Y31 group and rapamycin group are 1.22, 1.32 and 1.93 respectively.

The rapalogs or pharmaceutically acceptable salts thereof according to the present invention not only exhibit the above said anti-tumor activities and good pharmacokinetic parameters, but also maintain an immunosuppressive activity comparable or superior to that of rapamycin. Using rapamycin as control, systematic experiments on immunosuppressive bioacitivities were performed with compound Y31 as an example, and the results are shown in tables 10 to 12 and FIGS. 13 to 16.

(1) Effects of Rapamycin and Y31 on the Proliferation Activity of Spleen Lymphocytes of Normal Mice Induced by Mitogen/Allogeneic Antigen.

The results show that rapamycin and its derivative Y31 exhibit strong immunosuppressive activity in vitro, significantly suppressing the proliferation activity of the mitogen/allogeneic antigen induced lymphocytes (as shown in table 11 and FIG. 13).

(2) Effects of Rapamycin and Y31 on Delayed Type Hypersensitivity Reaction in Mice.

DNFB-induced DTH reaction is an allergic reaction mediated by Th1 cells and involving the activation of T cells and generation of various cytokines. The effects of the present compounds on DTH response were detected in BALB/c mice, and the results are shown in FIG. 14. The mice with DNFB-induced delayed type hypersensitivity reaction were taken as the group of model control, and had an average ear swelling degree of 0.175 mm. The mice in the group of positive control (Dex, 2 mg/kg) had an average swelling degree of 0.13 mm, which is significantly different from that of the model control group. The mice in the group of rapamycin had an average ear swelling degree of 0.076 mm, which is significantly different from that of the model control group. The mice in Y31 group had an average ear swelling degree of 0.129 mm, which is significantly different from the model control group.

The experimental results indicate that rapamycin and Y31 can remarkably inhibit the DNFB-induced delayed type hypersensitivity reaction in mice (as shown in FIG. 14).

(3) Effects of Rapamycin and Y31 on SRBC-Induced Specific Antibody-Producing Cells in Spleen Lymphocytes of Mice.

Rapamycin (1.5 mg/kg) and its derivative Y31 (1.5 mg/kg) by Intraperitoneal administration can significantly inhibit the amount of the SRBC-induced specific antibody-producing cells generated in the spleen of mice, and their inhibitory effects are superior to that of the positive control CsA, which indicates that they have significant inhibitory activity on the humoral immunity of mice (as shown in table 12).

(4) Pharmacodynamic Research of Rapamycin and Y31 on Acute Graft-Versus-Host Disease (aGVHD) of Mice.

The experimental results confirm that rapamycin and its derivative Y31 exhibit good therapeutic effects on acute graft-versus-host disease (aGVHD) in animal model (as shown in FIG. 15).

(5) The Therapeutic Effects of Y31 on Bovine type II Collagen-Induced Arthritis in DBA/1 Mice.

Subcutaneous injection of bovine type II collagen twice can induce arthritis in DBA/1 mice. Arthrocele appears at the fourth day after the attacking, and 100% of mice exhibit arthritis after one week, and the degree of arthrocele is progressively aggravated. The administration started at the $14^{th}$ day. The administration of Y31 can significantly reduce the onset degree of CIA, represented by the significant abatement of the arthrocele in mice's limbs and claws. Therefore, Y31 by oral administration can inhibit the onset of collagen-induced arthritis in DBA/1 mice (as shown in FIG. 16).

The rapalogs provided by the present invention exhibit excellent anti-tumor activities and immunosuppressive activities with good pharmacokinetic parameters, and the preparation method thereof is simple with good operability and high yield. Therefore, the rapalogs of the present invention has a good prospect in the development of drugs.

BEST MODE FOR CARRYING OUT THE INVENTION

Figure 1:
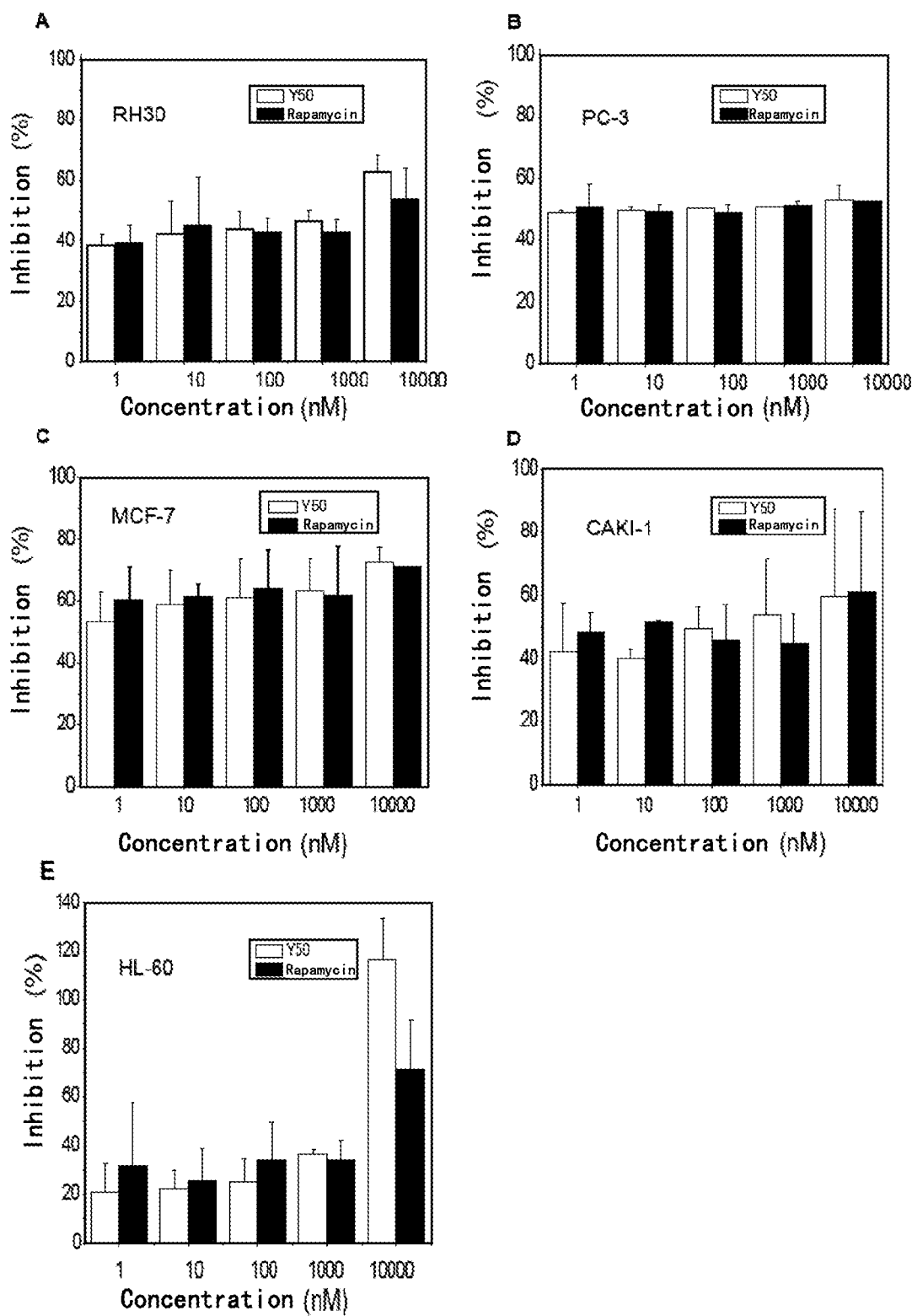
FIG. 1 is histograms illustrating the inhibitory effects of the compound Y50 at different concentrations on the growth of Rh30 (human rhabdomyosarcoma, A), PC-3 (human prostate cancer, B), MCF (human breast cancer, C), CAK-1 (human renal cell cancer, D) and HL-60 (human leucocythemia, E) cells.

The present invention will be further described with reference to the following specific examples, but the invention is not limited thereto.

Preparation Examples for the Rapalogs

In following examples, the routine post-treatment includes the following steps. After completion of the reaction, an appropriate amount of water was added into the reaction mixture, and then the organic and aqueous phases were separated. After the aqueous phase was sufficiently extracted by the organic solvent, the organic phase was combined, and if necessary, washed by 5% HCl solution and/or saturated NaHCO$_3$ solution, water and saturated saline respectively. Thereafter, the organic phase was dried over anhydrous Na$_2$SO$_4$ or anhydrous MgSO$_4$, filtrated and evaporated to dryness to obtain a crude product, which was then separated and purified by column chromatography to give the final product.

In following preparation examples, NMR was conducted on a Mercury-Vx 600M instrument manufactured by Varian with calibration of δ H/C 7.26/77.0 ppm (CDCl$_3$). The reagents were mainly provided by Shanghai Chemical Reagent Co. Ltd., and the products were purified by column chromatography with a silica gel of 200-300 mesh, wherein, the silica gel used in the column chromatography was a wide pore type (model ZLX-II), which was manufactured by Branch of Qingdao Haiyang Chemical Co. Ltd.

Preparation Example 1

Preparation of Compounds Y230, Y72 and Y50

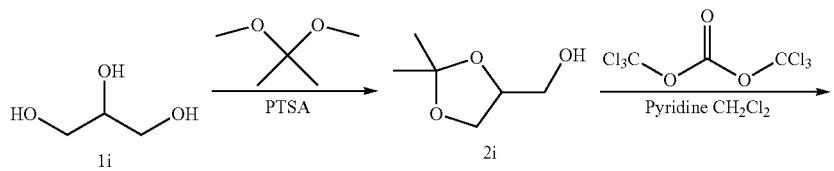

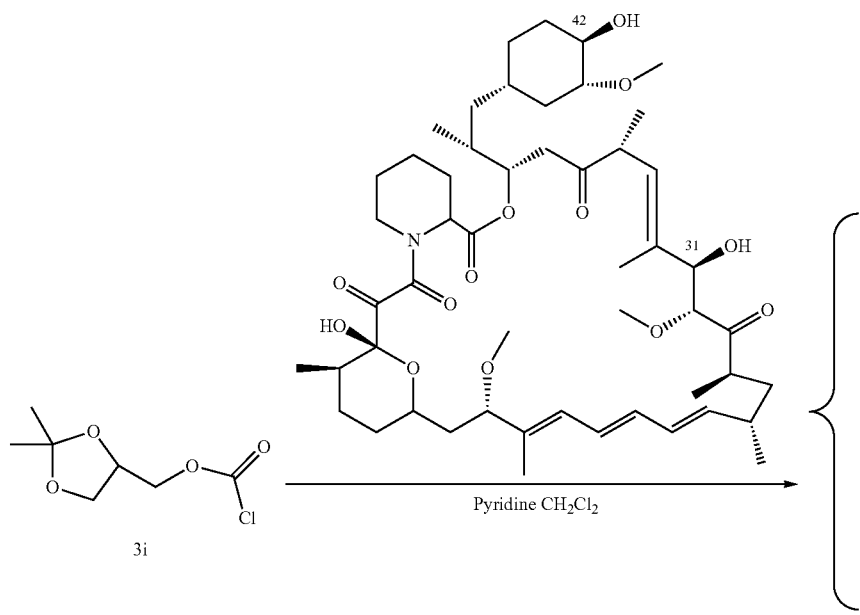

-continued

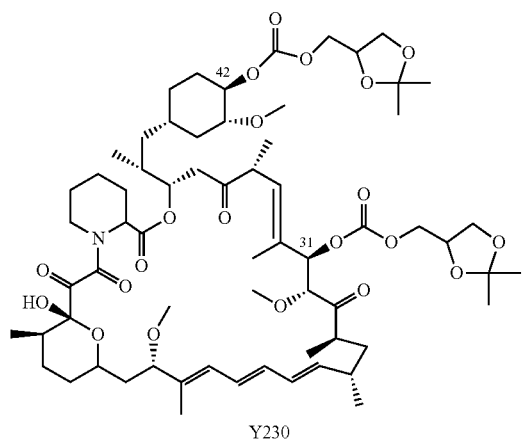

Y230

+

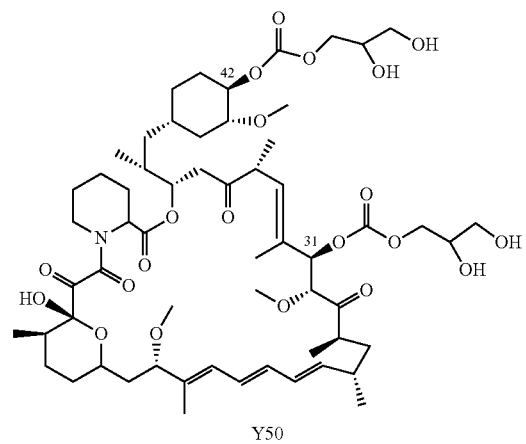

Y50

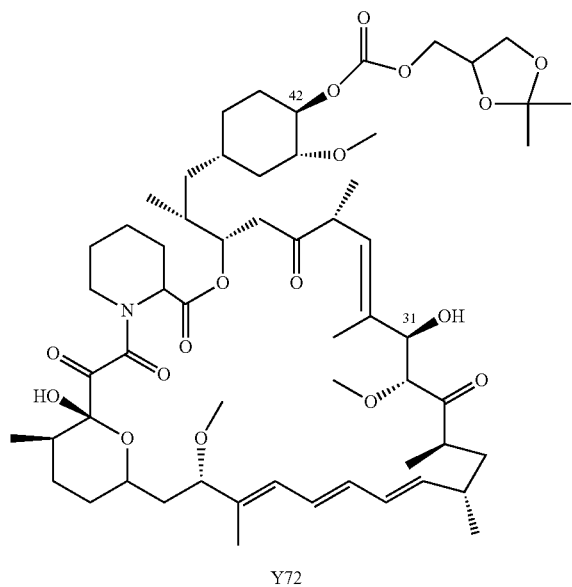

Y72

276 mg (3 mmol) of glycerol was dissolved in 2 ml of DMSO, and under a nitrogen atmosphere, 0.44 ml of 2,2-dimethoxy propane was injected and a catalytic amount of p-toluenesulfonic acid was further added therein. At room temperature, the mixture was stirred for several hours, and the reaction was traced by TLC until it was completed. And after a routine work-up, a liquid product 21 (total weight: 173 mg) was obtained.

173 mg of the compound 21 (1.31 mmol) and 130 mg (0.44 mmol) of triphosgene were added into a 50 ml round bottomed flask, and 25 ml of double distilled $CH_2Cl_2$ was injected therein under a nitrogen atmosphere, followed by dropwise addition of 170 μl (1.31 mmol) of dry pyridine under ice-water bath. After the dripping, the mixture was warmed up to room temperature naturally and the reaction continued for 2 hours. After that, 200 mg (0.22 mmol) of rapamycin and further 0.2 ml of pyridine were added therein. The reaction was traced by TLC until it was completed, and then the reaction mixture was neutralized to be faintly acidic by adding 1N HCl in the round bottomed flask. The mixture was extracted by dichloromethane, and the dichloromethane extract was washed by water and saturated saline, dried over anhydrous magnesium sulfate, and concentrated. The residue was purified by column chromatography eluting with petroleum ether/acetone (volume ratio, 5:1) to give a compound Y230 (total weight: 240 mg) with a compound Y72 (20 mg) as a by-product.

240 mg of the compound Y230 was dissolved in 3 ml THF, and at a temperature of 0-5° C., 1.7 ml of $2N H_2SO_4$ was added dropwise therein. The reaction was traced by TLC until it was completed, and then the reaction mixture was neutralized to be weak basic by adding 5% $NaHCO_3$. The mixture was extracted with ethyl acetate, and the ethyl acetate extract was washed by saturated saline, dried over anhydrous magnesium sulfate, and concentrated under reduced pressure. The residue was purified by rapid column chromatography eluting with petroleum ether/acetone (volume ratio, 1:1) to give a compound Y50 (total weight, 120 mg; overall yield, 38%).

| Serial Number | Structure | ¹HNMR (CDCl₃, 600 MHz) data |
|---|---|---|
| Y230 | 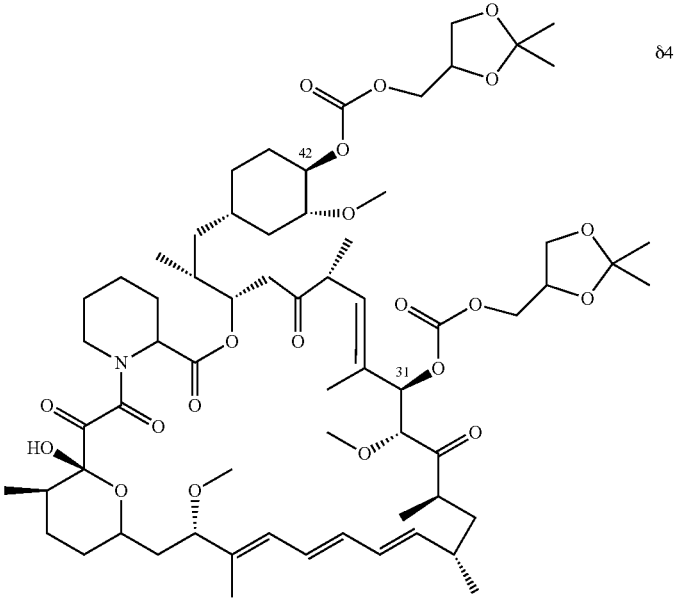 Y230 | δ5.12-5.18(m, 1H), δ4.52(m, 1H), δ4.26-4.34(m, 2H), δ4.02-4.20(m, 6H), δ3.72-3.82(m, 2H), δ1.36(s, 3H), δ1.37(s, 3H), δ1.40(s, 3H), δ1.38(s, 3H). |
| Y72 | 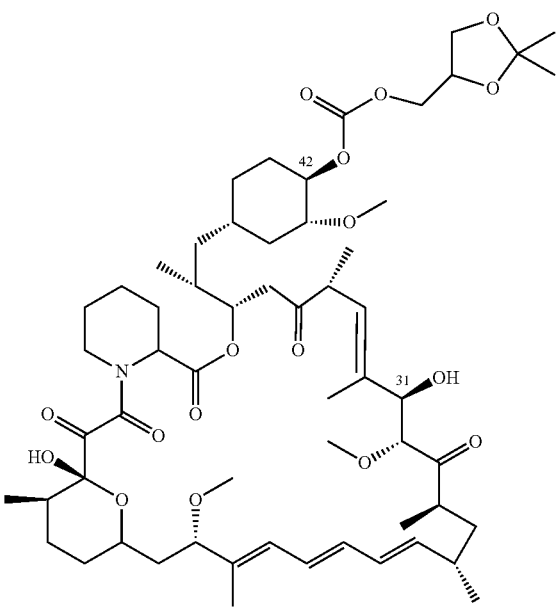 Y72 | δ4.50-4.56(m, 1H), δ4.35-4.40(m, 1H), δ4.15-4.23(m, 2H), δ4.08-4.13(m, 1H), δ3.78-3.82(m, 1H), δ1.37(s, 3H), δ1.43(s, 3H) |

| Serial Number | Structure | $^1$HNMR (CDCl$_3$, 600 MHz) data |
|---|---|---|
| Y50 | 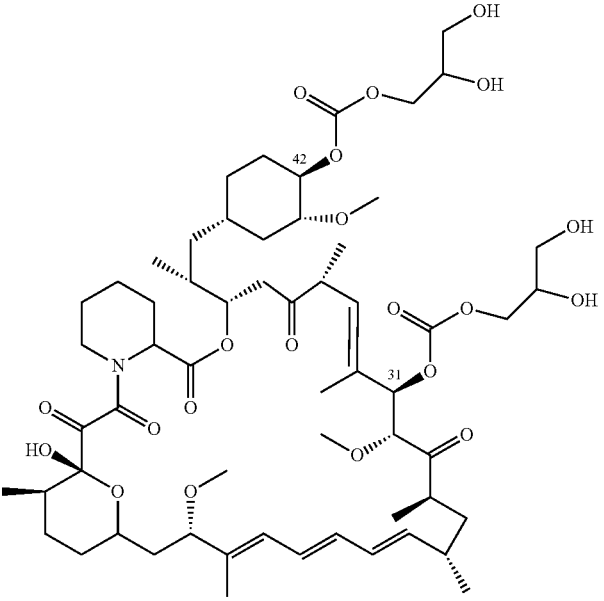 Y50 | δ5.12-5.16(m, 1H), δ4.42-4.54(m, 1H), δ4.17-4.24(m, 3H), δ4.08-4.13(m, 1H), δ3.85-3.96(m, 2H), δ3.50-3.76(m, 4H) |
Preparation Example 2
Preparation of Compound Y31
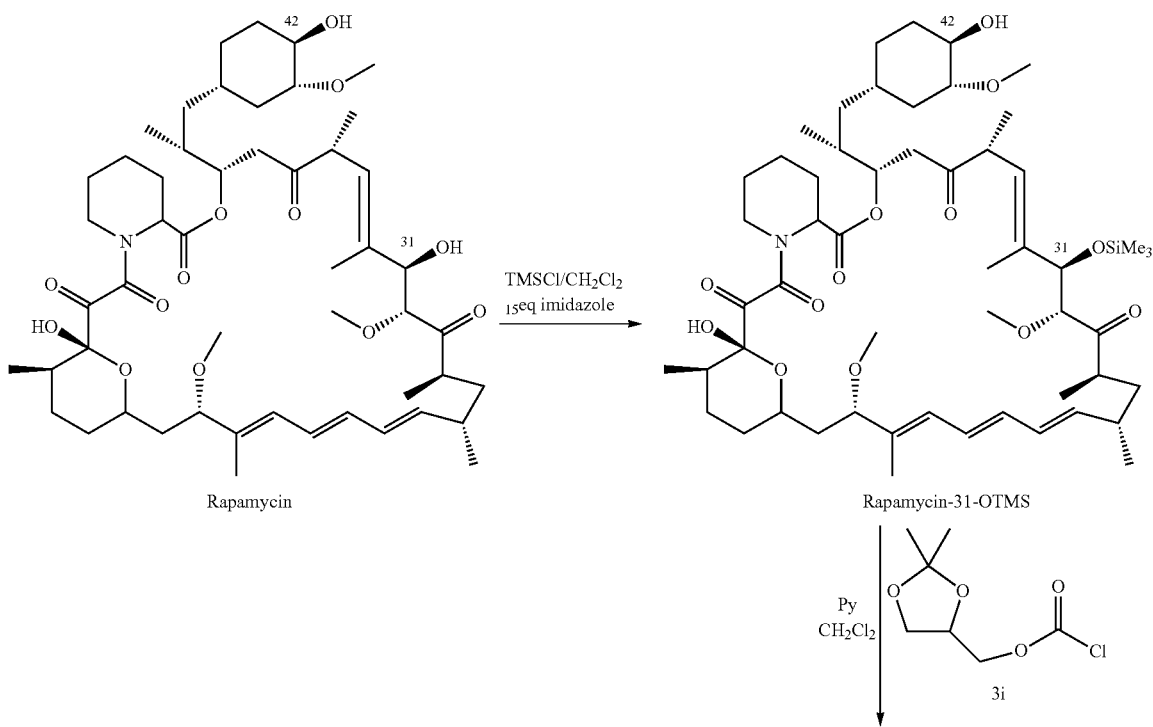

-continued

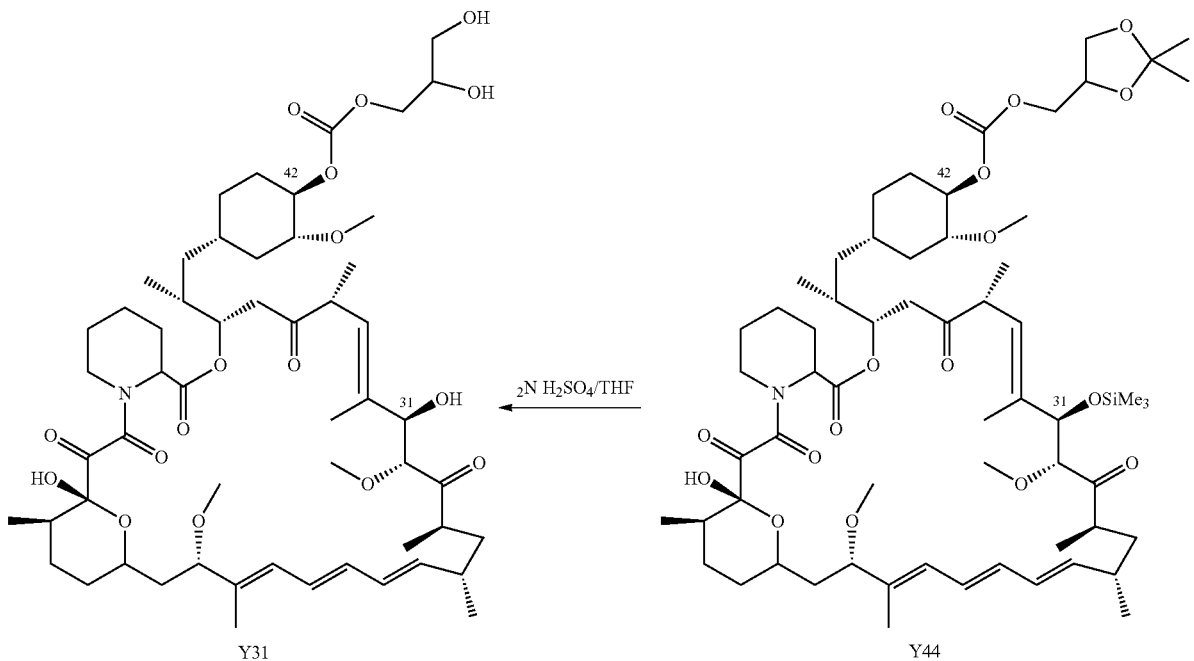

400 mg (0.44 mmol) of rapamycin and 449 mg (6.6 mmol) of imidazole were dissolved in 20 ml of double-distilled $CH_2Cl_2$, and 0.22 ml (1.76 mmol) of trimethyl chlorosilane was added dropwise therein. Then, the reaction was traced by TLC, and stirred for about 6 hours. The reaction mixture was concentrated under reduced pressure, and the residue was purified by column chromatography eluting with petroleum ether/acetone (volume ratio, 4:1) to give the rapamycin-31-OTMS (total weight: 277 mg).

573 mg of the compound 31 (4.34 mmol) and 453 mg (1.53 mmol) of triphosgene were added into a 50 ml round bottomed flask, and 30 ml of double-distilled $CH_2Cl_2$ was added therein under a nitrogen atmosphere, followed by dropwise addition of 377 μl (4.67 mmol) of dry pyridine under ice-water bath. After the dripping, the mixture was warmed up to room temperature naturally and the reaction continued for 2 hours. After that, 277 mg (0.28 mmol) of rapamycin-31-OTMS was added therein. The reaction was completed 4 hours later, as monitored by TLC. The reaction mixture was neutralized to be weak acidic by adding 1N HCl, extracted by dichloromethane. The dichloromethane extract was washed by water and saturated saline, dried over anhydrous magnesium sulfate, and concentrated. The residue was purified by column chromatography eluting with petroleum ether/acetone (volume ratio, 4:1) to give a compound Y44 (total weight: 240 mg).

240 mg of the compound Y44 was dissolved in 4 ml of THF, and at a temperature of 0-5° C., 1.7 ml of $2NH_2SO_4$ was added dropwise therein. The reaction was traced by TLC until the reaction was completed, and then the reaction mixture was neutralized to be weak basic by adding 5% $NaHCO_3$. The mixture was extracted with ethyl acetate, and the ethyl acetate extract was washed by saturated saline, dried over anhydrous magnesium sulfate, and concentrated under reduced pressure. The residue was purified by column chromatography eluting with petroleum ether/acetone (volume ratio, 1.5:1) to give a compound Y31 (total weight, 120 mg).

| Serial Number | Structure | $^1$H NMR (CDCl$_3$, 600 MHz) data |
|---|---|---|
| Y31 | 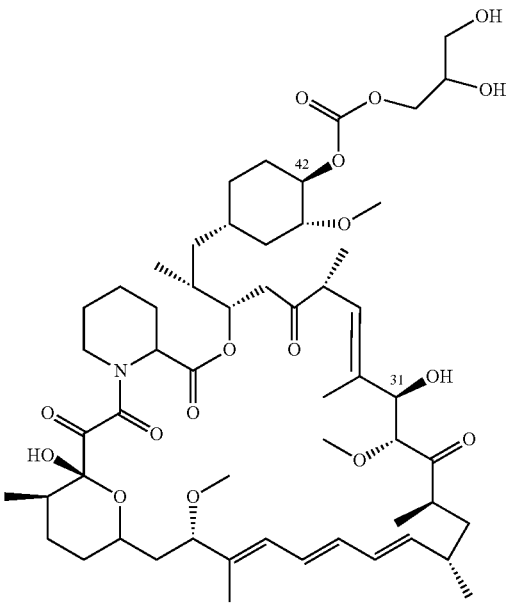 Y31 | δ4.45-4.56(m, 1H), δ4.15-4.30(m, 2H), δ3.90-3.97(m, 1H), δ3.70-3.78(m, 1H), δ3.58-3.64(m, 1H) |

Preparation Example 3

Preparation of Compound Y31-1

For the preparation of rapamycin-31-OTMS, reference was made to the preparation example 2.

200 mg (0.2 mmol) of rapamycin-31-OTMS and 206 mg (3 mmol) of imidazole were added in a 25 ml round bottomed flask, and then 7 ml of DMF was injected and 184 mg (1.22 mmol) of dimethyl-t-butyl chlorosilane (TBSCl) was added therein. The reaction was traced by TLC, and performed for 48 hours. After that, the reaction mixture was diluted by water and extracted with ethyl acetate, and then the ethyl acetate extract was washed by water and saturated saline, dried over anhydrous magnesium sulfate. The residue was purified by column chromatography eluting with petroleum ether/ethyl acetate (volume ratio, 3:1) to give a compound Y028 (total weight: 120 mg).

173 mg of the compound 31 (1.31 mmol) and 130 mg (0.44 mmol) of triphosgene were added into a 50 ml round bottomed flask, and 25 ml of double-distilled CH$_2$Cl$_2$ was added therein under a nitrogen atmosphere, followed by dropwise addition of 170 μl (1.31 mmol) of dry pyridine under ice-water bath. After the dripping, the mixture was warmed up to room temperature naturally and the reaction continued for 2 hours. After that, 120 mg (0.12 mmol) of Y028 and further 0.2 ml of pyridine were added therein. The reaction was traced by TLC until it was completed, and then the reaction mixture was neutralized to be weak acidic by adding 1N HCl in the round bottomed flask. The mixture was extracted by dichloromethane, and the dichloromethane extract was washed by water and saturated saline, dried over anhydrous magnesium sulfate, and concentrated. The residue was purified by column chromatography eluting with petroleum ether/acetone (volume ratio, 3:1) to give a compound Y86 (total weight: 100 mg).

100 mg of the compound Y86 was dissolved in 1.5 ml of THF, and at a temperature of 0-5° C., 0.8 ml of 2NH$_2$SO$_4$ was added dropwise therein. The reaction was traced by TLC until it was completed, and then the reaction mixture was neutralized to be weak basic by adding 5% NaHCO$_3$. The mixture was extracted with ethyl acetate, and the ethyl acetate extract was washed by saturated saline, dried over anhydrous magnesium sulfate, and concentrated under reduced pressure. The residue was purified by rapid column chromatography eluting with petroleum ether/acetone (volume ratio, 1:1) to give a compound Y31-1 (total weight: 80 mg).

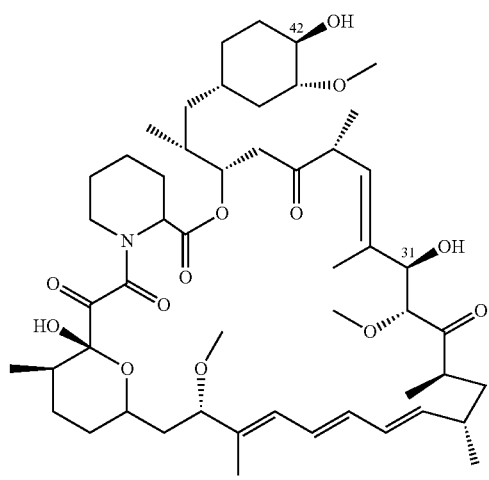
27
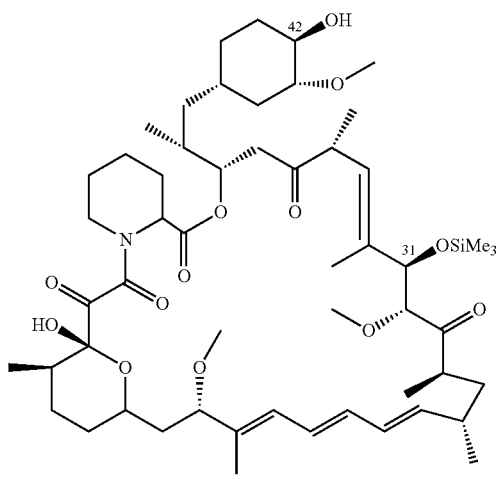
28
Rapamycin-31-OTMS
TMSCl / imidazole / CH₂Cl₂
TBSCl / imidazole / DMF
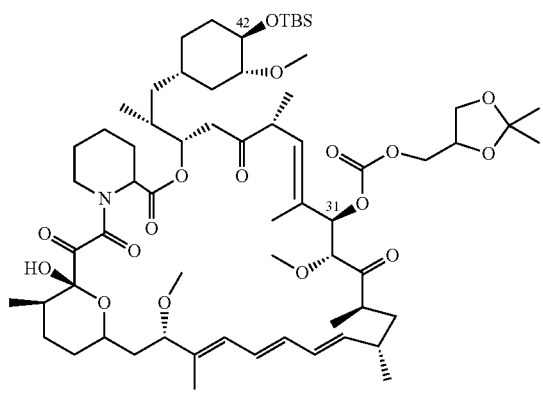
Y86
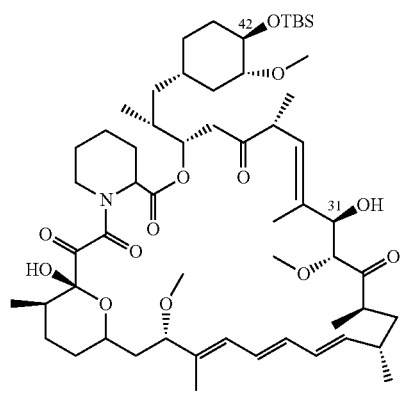
Y028
Py/CH₂Cl₂
3i
2N H₂SO₄
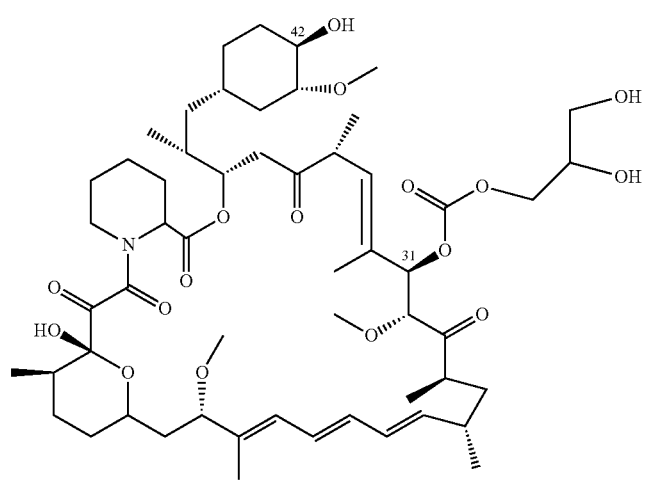
Y31-1

| Serial Number | Structure | $^1$H NMR (CDCl$_3$, 600 MHz) data |
|---|---|---|
| Y31-1 | Y31-1 | δ5.12-5.18(m, 1H), δ4.20-4.26(m, 1H), δ4.08-4.15(m, 1H), δ3.85-3.95(m, 1H), δ3.60-3.70(m, 1H), δ3.50-3.58(m, 1H) |

Biologic Experimental Example

Example 1

Experiments for Evaluating the Antineoplasmic Activity at a Cellular Level

I. The Inhibitory Effects of Y50 on the Growth of Rh30, PC-3, MCF-7, CAKI-1 and HL-60 Cells:

After Rh30 cells were treated by the compound at different concentrations, the cell survival rate was detected by SRB method.

The above various kinds of tumor cells in logarithmic growth phase were inoculated on a 96-well plate with 90 μl per well, and allowed to attach for 24 hours, followed by the addition of the compound with 10 μl per well. For each concentration, the test was carried out in triplicate wells, and included a control well containing the aqueous medium of normal saline at the corresponding concentration and a blank well without cells for zeroing. The tumor cells were cultured for 72 hours at 37° C. and 5% CO$_2$, and then the culture medium was removed. The cells were fixed with cold 10% TCA (trichloroacetic acid) at 4° C. for 1 hour, then washed with distilled water for 5 times, and dried at room temperature, followed by addition of a SRB (Sigma) solution (4 mg/ml) in 1% glacial acetic acid at 100 μl per well. The cells were stained at room temperature for 15 min, and the supernatant was removed. The plate was washed by 1% acetic acid for 5 times and dried at room temperature. Finally, Tris-solution was added at 150 μl per well, and the A value was measured at a wavelength of 520 nm on an ELISA Reader. The growth inhibition of the compound against the tumor cells was calculated according to the following equation:

Growth inhibition (%)=($A_{520\ control}$−$A_{520\ treated}$)/$A_{520\ control}$×100%

Results as demonstrated in FIG. 1 showed that Y50 exhibited inhibitory effects against the above various kinds of tumor cells comparable to those of rapamycin.

Figure 2:
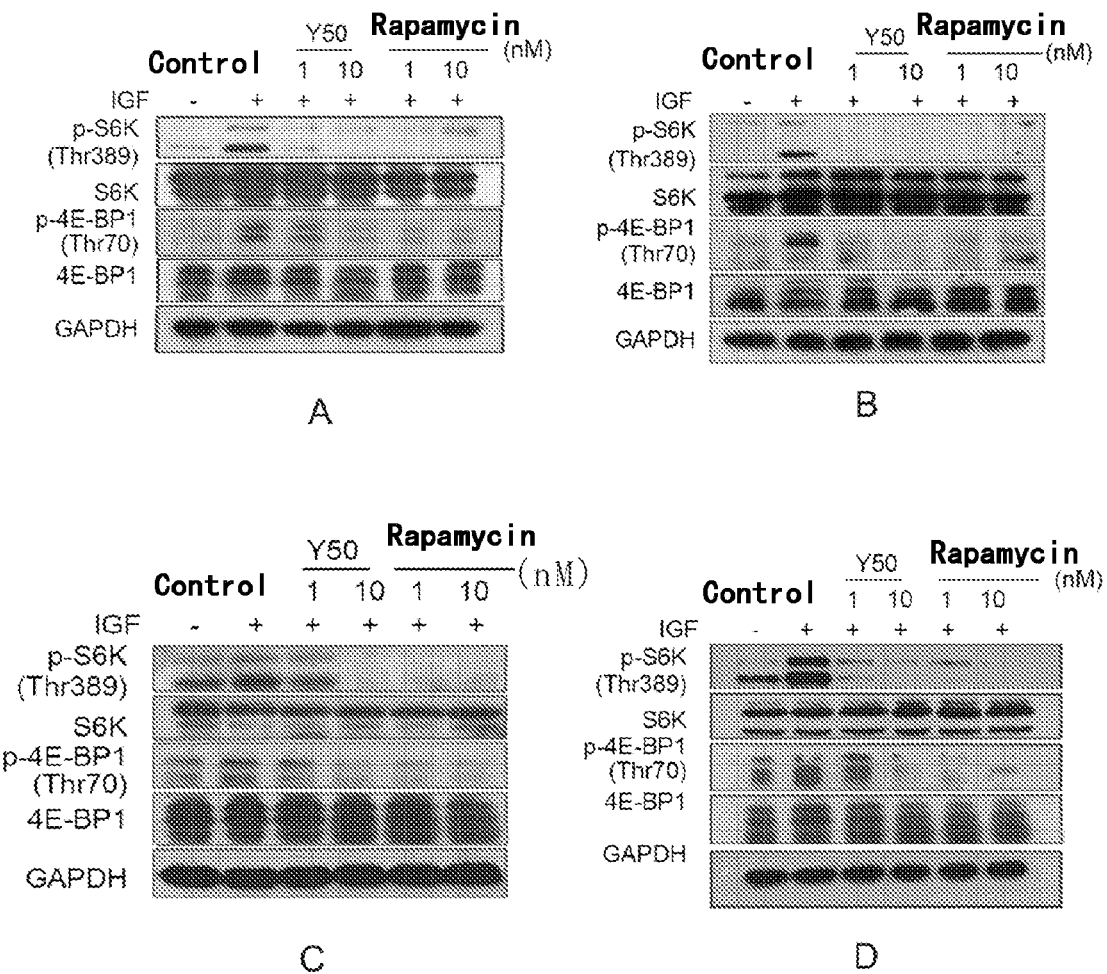
FIG. 2 is photographs illustrating the effects of Y50 on the phosphorylation levels of p70S6K and 4E-BP1 in Rh30, PC-3, MCF-7 and CAK-1 cells.

II. The Inhibitory Effects of Y50 on Phosphorylation Levels of p70S6K and 4E-BP1 in Rh30, PC-3, MCF-7 and CAKI-1 Cells Cells were inoculated on a 12-well plate with given densities and allowed to attach overnight. Then the medium was changed to a serum-free one. After starved for 24 hours, the cells were treated with the compound at corresponding concentrations for 1 hour, and then stimulated by IGF for 10 min. The cells were collected, and the phosphorylation levels of p70S6K and 4E-BP1 in the cells were measured by using Western blotting. Results as demonstrated in FIG. 2 showed that Y50 could concentration-dependently suppress the ability of mTOR for catalyzing the phosphorylation of the downstream substrates thereof in various kinds of tumor cells. At the same concentration, Y50 has comparable inhibitory effects to those of rapamycin.

III. Experiments for Evaluating the Binding Abilities of the Compounds Y50 and Y31 with the Target Protein FKBP-12

1. Reagents and Instruments:
(1) FKBP-12 protein was purchased from sigma Co.
(2) HBS-EP buffer solution (10 mM Hepes, 150 mM NaCl, 3.4 mM EDTA, 0.005% (v/v) surfactant P20, pH 7.4)
(3) Activating reagents EDC and NHS, and blocking reagents Ethanolamine, etc., were purchased from BIACORE AB Co. (Uppsala, Sweden).
(4) BIAcore 3000 and CM5 chip were purchased from BIACORE AB Co. (Uppsala, Sweden).

2. Experimental Protocol:
(1) The coupling with FKBP-12 protein
(2) Tubulin protein was coupled to the FC2 channel on CM5 chip by using the Wizard for amino-coupling in Biacore 3000 controlling soft. 3.3 g/L of FKBP-12 protein was diluted with 10 mM NaAC (pH 4.6) to 66 μg/ml. The surface of the chip was washed by injecting a mixture of 0.1M 1-(3-dimethylaminopropyl)-3-ethylcarbodiimide hydrochloride (EDCI) and 0.1M N-hydroxysuccinimide (NHS) (1:1) at a flow rate of 20 μL/min for 7 min. After that, the protein solution was injected, and then a 1M cholamine (pH 8.5) solution was fed for 7 min to block the activated surface of the chip. Preliminary screening and pharmacokinetic tests on the compounds The binding abilities of small molecular compounds with FKBP-12 protein were evaluated by SPR (surface plasma resonance). The stock solution of the compound was 10 mM, and was diluted by HBS-EP buffer solution at given ratios. Pharmacokinetic tests were carried out by the Wizard for kinetic analysis in Biacore 3000 controlling soft. The resulted data were fitted by 1:1 Langmuir binding model or stability model in Biacore 3000 analytical soft to obtain the exact kinetic and thermodynamic constants.

Figure 8:
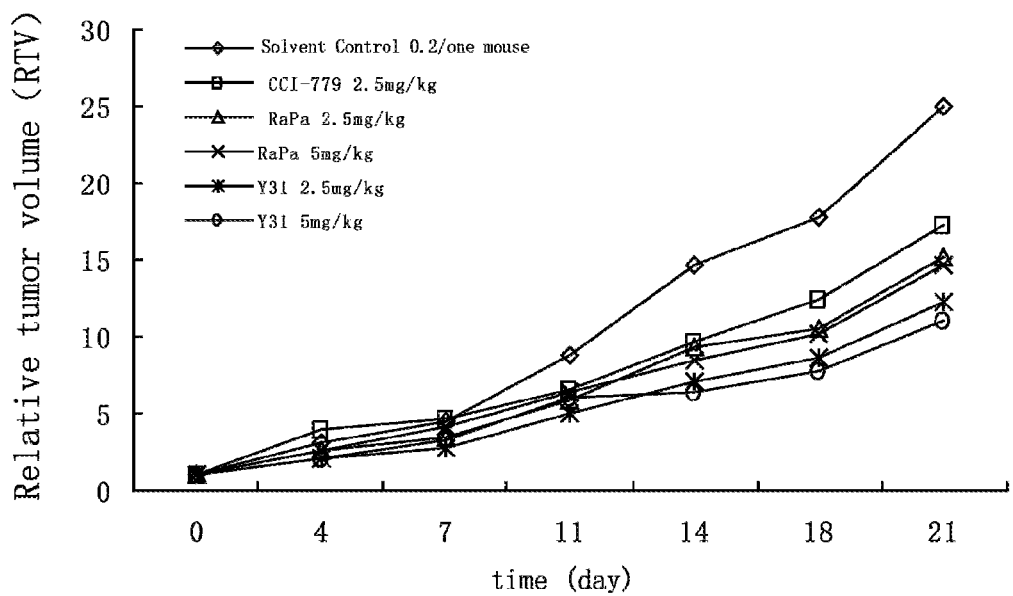
FIG. 8 illustrates the experimentally therapeutic effects of the compounds Y31, CCI-779 and rapamycin on human osteosarcoma U2SO xenograft on nude mice.
Figure 9:
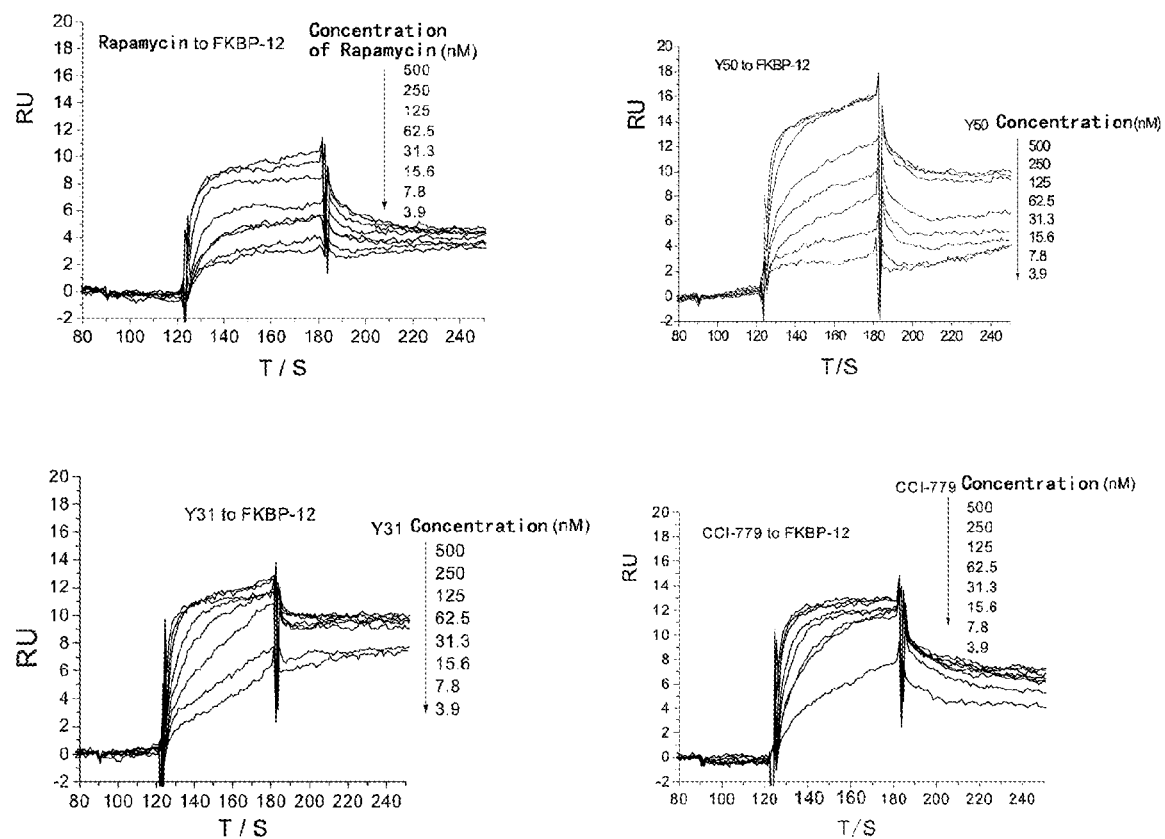
FIG. 9 is a graph illustrating the bonding activities of small molecule compounds with protein FKBP-12 determined by SPR (surface plasma resonance).
Figure 10:
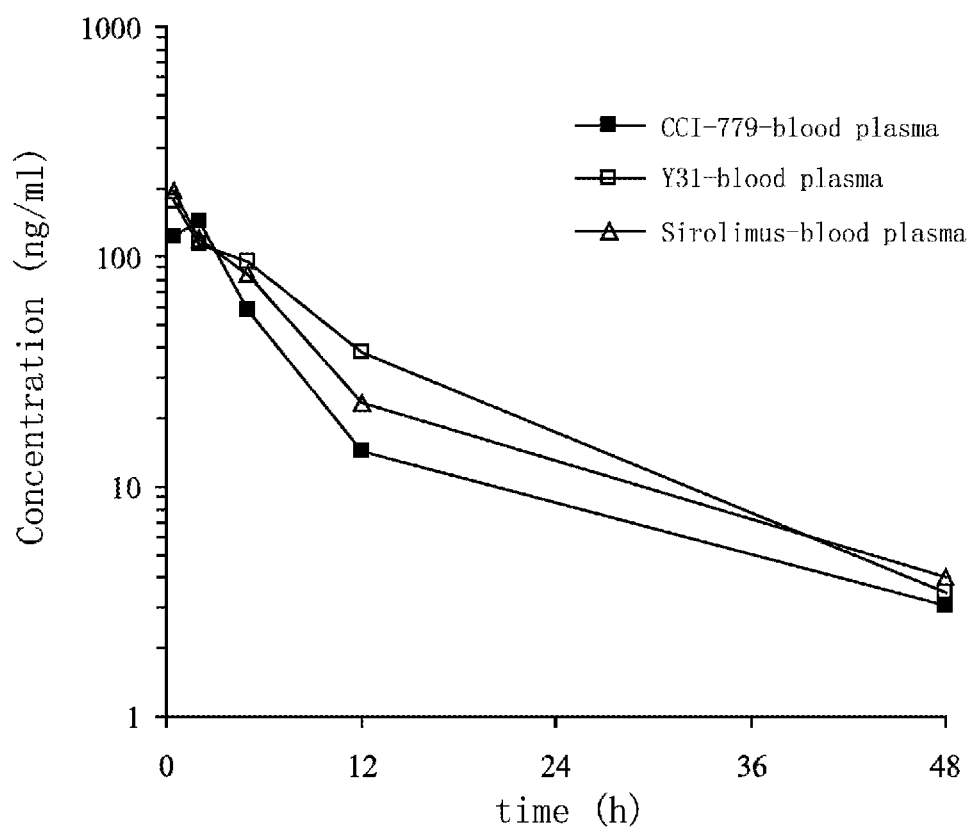
FIG. 10 is a graph illustrating the rapamycin concentration vs time curve in plasma after the administration of Y31, CCI-779 and rapamycin to nude mice respectively.
Figure 11:
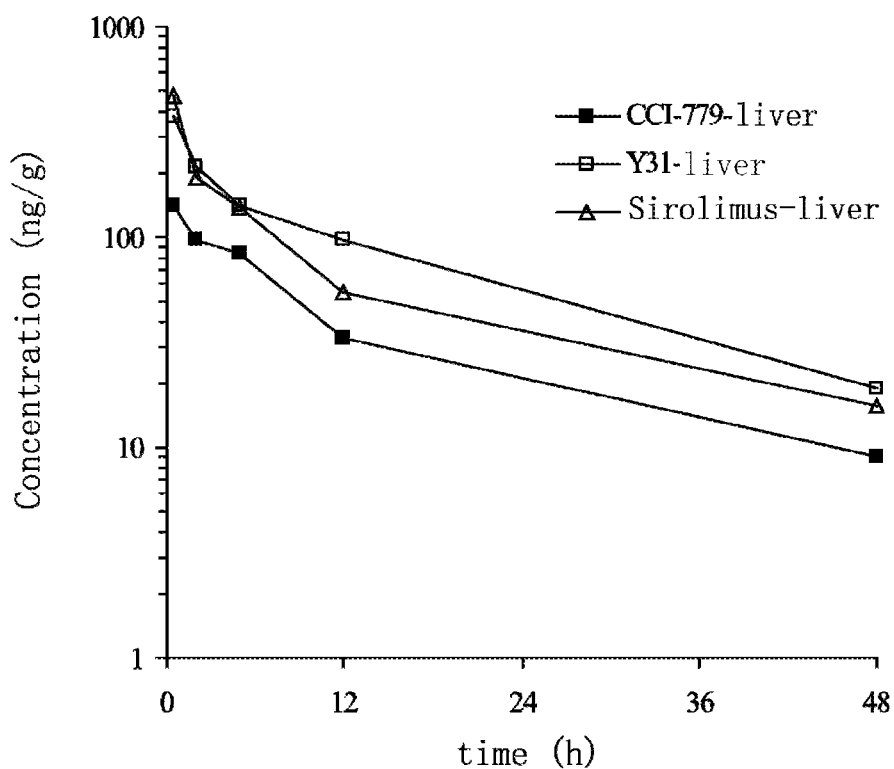
FIG. 11 is a graph illustrating the rapamycin concentration vs time curve in liver after the administration of Y31, CCI-779 and rapamycin to nude mice.
Figure 12:
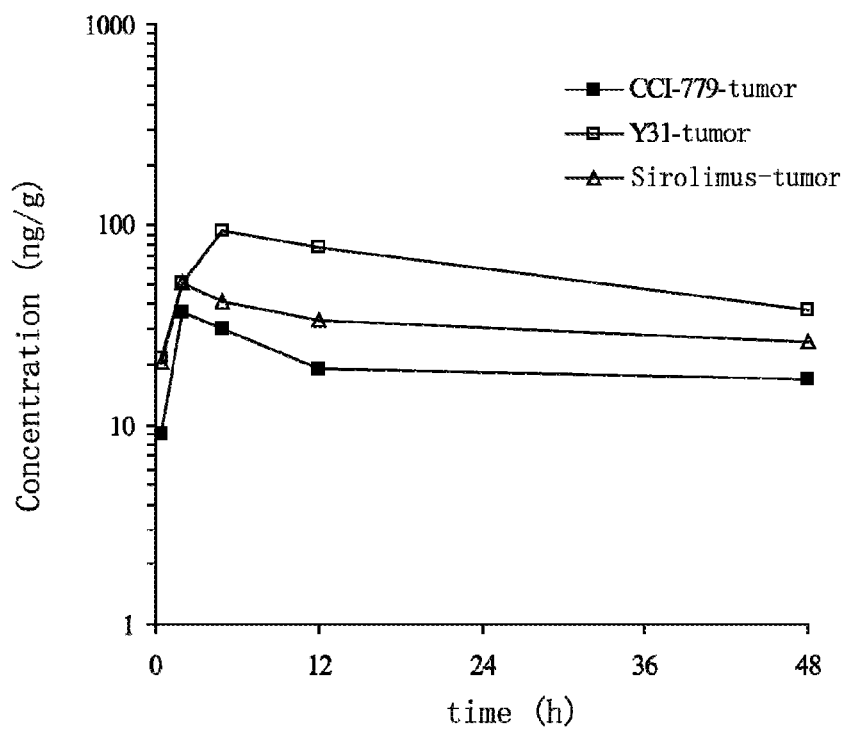
FIG. 12 is a graph illustrating the rapamycin concentration vs time in tumor tissue after the administration of Y31, CCI-779 and rapamycin to nude mice.

(3) Results of SPR tests (as shown in table 1 and FIG. 8):

1. Rapamycin, CCI-779, Y50 or Y31 can concentration-dependently bind with FKBP12. Y50 and Y31 exhibited higher $R^U$ (Response Unit) than that of rapamycin at the same concentration, which indicates that Y50 or Y31 have stronger binding abilities with FKBP-12 than that of rapmycin at the same concentration.

2. The concentration to reach the saturation state for the binding of Y50 or Y31 with FKBP12 is lower than that for rapamycin.

3. Y50 and Y31 have a smaller dissociation rate with FKBP12 than that of rapamycin, and also CCI-779. Y50 and Y31 also have a smaller dissociation constant than those of rapamycin and CCI-779.

TABLE 1

The binding abilities of small molecular compounds with FKBP-12 protein measured by SPR (surface plasma resonance)

| Analyte | FKBP12 | | | |
|---|---|---|---|---|
| | $k_{on}[M^{-1}S^{-1}]$ | $k_{off}[S^{-1}]$ | $K_D [M]$ | $\chi^2$ |
| Rapamycin | $2.93 \times 10^6$ | $5.73 \times 10^{-3}$ | $1.96 \times 10^{-9}$ | 0.438 |
| Y50 | $5.24 \times 10^5$ | $0.14 \times 10^{-3}$ | $0.26 \times 10^{-9}$ | 2.33 |
| Y31 | $1.05 \times 10^6$ | $0.11 \times 10^{-3}$ | $0.10 \times 10^{-9}$ | 2.41 |
| CCI-779 | $4.26 \times 10^6$ | $4.35 \times 10^{-3}$ | $1.02 \times 10^{-9}$ | 0.982 |

Example 2

Experiments for Evaluating the Antineoplasmic Activity at an Animal Level

Experimental object: to evaluate the growth inhibitory effect of Y50 against human rhabdomyosarcoma RH-30 xenograft on nude mice.

Testing sample: Y50 was formulated to an oral preparation in a solvent of 5% Tween 80, 5% PEG400 and DDW.

Positive control: rapamycin was formulated to an oral preparation in a solvent of 5% Tween 80, 5% PEG400 and DDW.

Dosage: for 2 dosage groups, Y50 was orally administered once daily at 5 and 10 mg/kg respectively; and rapamycin was orally administered at the same dosages as those of Y50.

Animals: BALB/cA nude mice, male, 40-45 days old, body weight: 21±2 g, provided by Shanghai Institute of Materia Medica, Chinese Academy of Sciences. License No.: SCXK (Shanghai) 2004-0002. Animal number in each group: 6 in negative control group, and 6 in administration group.

Xenograft: human rhabdomyosarcoma RH-30 xenograft on nude mice, which was established by inoculating human habdomyosarcoma RH-30 cell line on nude mice subcutaneously. The amount of inoculated cells was $5 \times 10^6$. After the xenograft was formed by inoculation, it was used after passed for 3 generations in nude mice.

Experimental procedure: tumor tissue in productive phase was cut into nubs of about 1.5 mm$^3$. Under sterile conditions, the nubs were inoculated subcutaneously in right axillary fossa of the nude mice. The diameter of the xenograft on nude mice was measured by a vernier caliper. When the tumors grew up to 100-200 mm$^3$, the animals were divided randomly into groups. Mice in experimental groups were administered orally once daily for 3 weeks. The positive control, rapamycin, was administered in the same way with the same dosage for 3 weeks. And mice in negative control groups were orally administered the solvent with 0.2 ml per mouse. The diameter of the tumor and weight of the mice were measured twice a week. The tumor volume (TV) was calculated through the following equation: TV=½×a×b$^2$, wherein, a is length and b is width. And relative tumor volume (RTV) was calculated based on the measured results through the following equation: RTV=$V_t N_o$, wherein, $V_o$ is the tumor volume measured at a time (i.e. $d_o$) when the mice were grouped, and $V_t$ is the tumor volume at each measurement. The evaluation index for the anti-tumor activity was the relative tumor proliferation rate T/C (%).

The calculation equation was as follows:

T/C(%)=($T_{RTV}/C_{RTV}$)×100, wherein, $T_{RTV}$ is the RTV of the therapeutic Group and $C_{RTV}$ is the RTV of the negative control group.

Evaluation standard for the curative effect: T/C (%)>60% indicates ineffective, while T/C (%)<=60 with a statistic result of p<0.05 represents effective.

Figure 3:
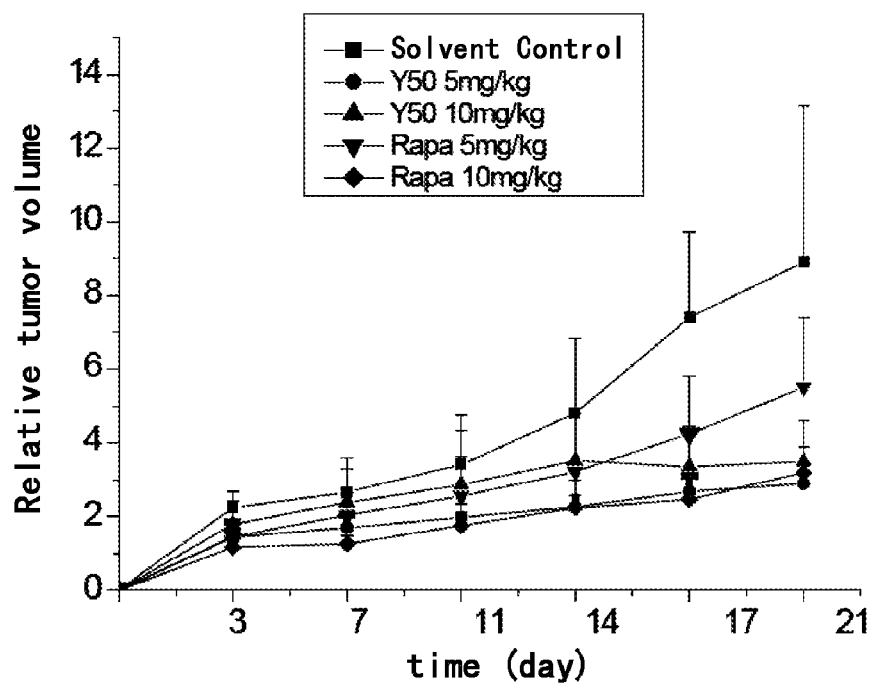
FIG. 3 is a graph illustrating the inhibitory effects of the compound Y50 on the growth of human rhabdomyosarcoma Rh30 xenograft on nude mice.
Figure 4:
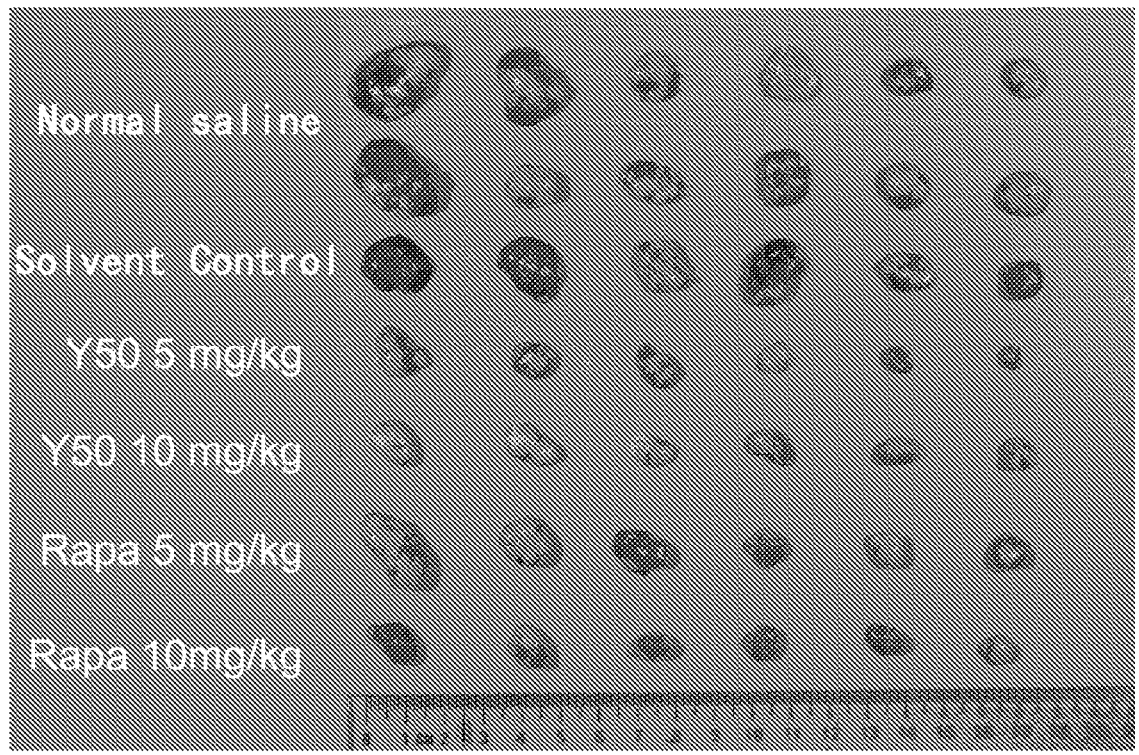
FIG. 4 is a photograph illustrating the inhibitory effects of the compound Y50 on the growth of human rhabdomyosarcoma Rh30 xenograft on nude mice.

Results: the growth inhibition of Y50 against human rhabdomyosarcoma RH-30 xenograft on nude mice was shown in Table 2 and FIGS. 3 and 4. The above experimental results demonstrated that the two dosage groups wherein Y50 were orally administered with 5 and 10 mg/kg respectively once daily for 3 weeks, exhibited significant growth inhibition against human rhabdomyosarcoma RH-30 xenograft on nude mice with T/C values of 32.5% and 32.9% respectively, which was comparable with that of the high dosage group of the positive control rapamycin. While, the low dosage (5 mg/kg) group of rapamycin did not exhibit apparent inhibition against the human rhabdomyosarcoma RH-30 xenograft on nude mice, and the T/C value thereof was 61.8%. No mice died in the experimental groups.

Conclusion: Y50 through oral administration has significantly superior growth inhibition against human rhabdomyosarcoma RH-30 xenograft on nude mice to that of rapamycin, as shown in table 2 and FIGS. 3 and 4.

TABLE 2 the experimental therapeutic effects of Y50 against human rhabdomyosarcoma RH-30 xenograft on nude mice

| Group | Dosage, Administration Manner | | Animal Number | | Body Weight (g) | | TV (mm$^3$) | | RTV | T/C (%) | P value |
|---|---|---|---|---|---|---|---|---|---|---|---|
| | | | start | end | start | end | $d_0$ | $d_{21}$ | | | |
| solvent control | 0.2 ml per mouse | p.o | 6 | 6 | 22.0 | 25.2 | 134 ± 49 | 1099 ± 462 | 8.9 ± 4.2 | | |
| Y50 | 5 mg/kg, 1-5 × 3 w | p.o | 6 | 6 | 22.2 | 25.8 | 132 ± 47 | 380 ± 146 | 2.9 ± 0.5 | 32.5 | <0.05 |

TABLE 2-continued the experimental therapeutic effects of Y50 against human rhabdomyosarcoma RH-30 xenograft on nude mice

| Group | Dosage, Administration Manner | | Animal Number | | Body Weight (g) | | TV (mm$^3$) | | RTV | T/C (%) | P value |
|---|---|---|---|---|---|---|---|---|---|---|---|
| | | | start | end | start | end | $d_0$ | $d_{21}$ | | | |
| Y50 | 10 mg/kg, 1-5 × 3 w | p.o | 6 | 6 | 23.0 | 26.0 | 130 ± 50 | 415 ± 71 | 3.5 ± 1.1 | 32.9 | <0.05 |
| rapamycin | 5 mg/kg, 1-5 × 3 w | p.o | 6 | 6 | 23.7 | 27.0 | 124 ± 65 | 650 ± 326 | 5.5 ± 1.8 | 61.8 | >0.05 |
| rapamycin | 10 mg/kg, 1-5 × 3 w | p.o | 6 | 6 | 23.3 | 25.7 | 136 ± 57 | 410 ± 142 | 3.1 ± 0.7 | 35.7 | <0.05 |

Figure 5:
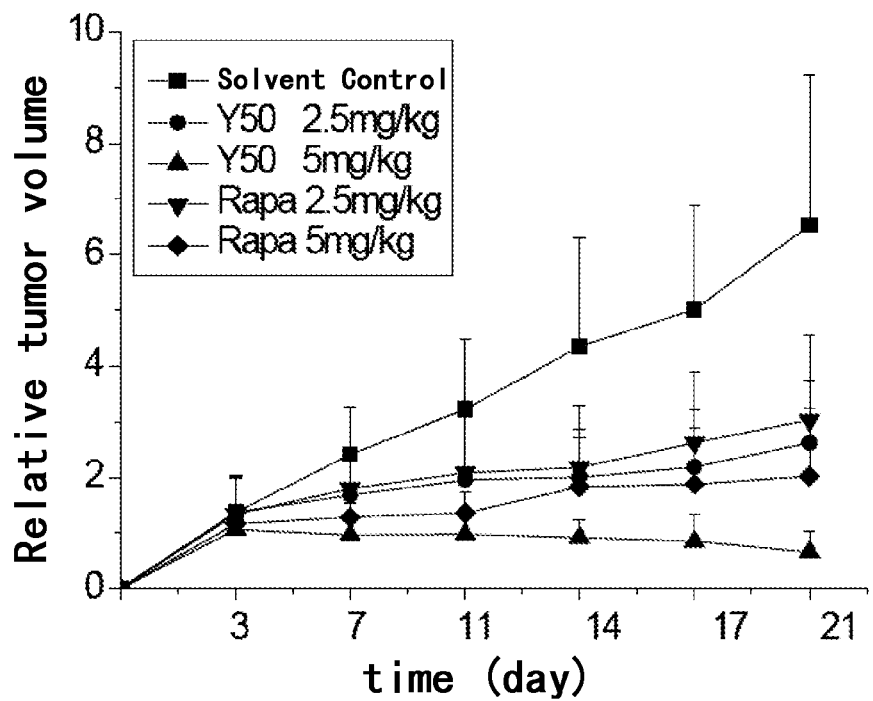
FIG. 5 is a graph illustrating the inhibitory effects of the compound Y50 on the growth of human prostate cancer PC-3 on nude mice.
Figure 6:
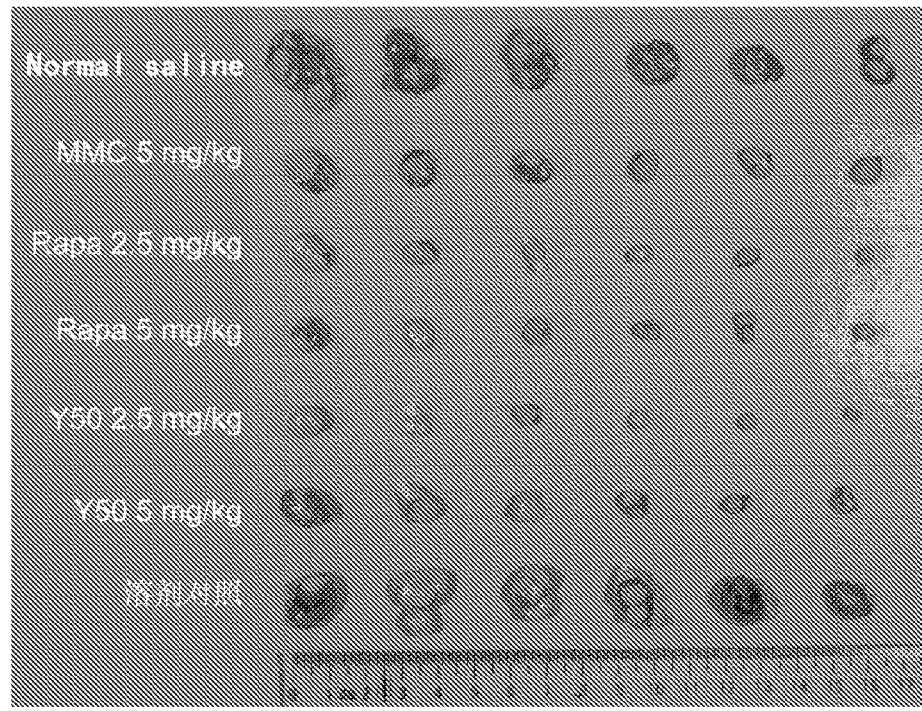
FIG. 6 is a photograph illustrating the inhibitory effects of the compound Y50 on the growth of human prostate cancer PC-3 on nude mice.

The growth inhibition of Y50 against human prostate cancer PC-3 xenograft on nude mice was observed by the same experimental protocol as the above. The results showed that Y50 through oral administration in different dosage groupshad significantly superior growth inhibition against human prostate cancer PC-3 xenograft on nude mice to those of rapamycin, wherein the T/C values of the Y50 groups were 10.0% and 40.2% respectively while the T/C values in the positive control groups with the corresponding dosage of rapamycin were 30.9% and 46.5% respectively, as shown in table 3 and FIGS. 5 and 6.

mice was observed by the same experimental protocol as the above. Y31, Y50 and Y31-1 through oral administration exhibited significant growth inhibition against human rhabdomyosarcoma RH-30 xenograft on nude mice. Y31 and Y50 showed superior growth inhibition against the above said tumor to that of rapamycin. Among them, rapamycin in low dosage (2.5 mg/kg) group exhibited unapparent growth inhibition against human rhabdomyosarcoma RH-30 xenograft on nude mice with a T/C value of 63.7%, while Y31 even at low dosage (2.5 mg/kg) could achieve a significant growth inhibition effect, which was markedly superior to those of

TABLE 3 the experimental therapeutic effects of Y50 against human prostate cancer xenograft on nude mice

| Group | Dosage, Administration Manner | | Body Number | | Animal Weight (g) | | TV (mm3) | | RTV | T/C (%) | P Value |
|---|---|---|---|---|---|---|---|---|---|---|---|
| | | | start | end | start | end | $d_0$ | $d_{21}$ | | | |
| Solvent Control | 0.2 ml per mouse, 1-5 × 3.5 w | p.o | 6 | 6 | 22.3 | 18.2 | 109 ± 47 | 629 ± 151 | 6.5 ± 2.7 | | |
| Y50 | 5 mg/kg, 1-5 × 3.5 w | p.o | 6 | 6 | 22.7 | 22.3 | 98 ± 42 | 70 ± 59 | 0.65 ± 0.4 | 10.0 | <0.01 |
| Y50 | 2.5 mg/kg, 1-5 × 3.5 w | p.o | 6 | 6 | 19.7 | 17.7 | 103 ± 35 | 273 ± 163 | 2.6 ± 1.1 | 40.2 | <0.01 |
| Rapamycin | 5 mg/kg, 1-5 × 3.5 w | p.o | 6 | 6 | 22.2 | 22.2 | 96 ± 38 | 170 ± 88 | 2.0 ± 1.2 | 30.9 | <0.01 |
| Rapamycin | 2.5 mg/kg, 1-5 × 3.5 w | p.o | 6 | 6 | 19.8 | 21.8 | 100 ± 39 | 277 ± 98 | 3.03 ± 1.5 | 46.5 | <0.05 |

TABLE 4 the experimental therapeutic effects of Y50, Y31, Y31-1 and rapamycin against rhabdomyoma RH-30 xenograft on nude mice

| Group | Dosage, Administration Manner | | Animal Number | | Body Weight (g) | | TV (mm$^3$) | | RTV | T/C (%) | P value |
|---|---|---|---|---|---|---|---|---|---|---|---|
| | | | start | end | start | end | d0 | d14 | | | |
| Control | 0.2 ml per mouse 1-5/2 w | po | 6 | 6 | 19.7 | 21.0 | 163 ± 74 | 701 ± 366 | 4.4 ± 1.5 | | |
| Solvent Control | 0.2 ml per mouse 1-5/2 w | po | 6 | 6 | 19.2 | 21.7 | 159 ± 59 | 718 ± 188 | 5.1 ± 2.3 | 116.8 | >0.05 |
| Y50 | 5 mg/kg, 1-5/2 w | po | 6 | 6 | 20.0 | 21.5 | 160 ± 47 | 323 ± 124 | 2.0 ± 0.5 | 46.6 | <0.05 |
| Y31 | 5 mg/kg, 1-5/2 w | po | 6 | 6 | 20.8 | 21.7 | 160 ± 53 | 316 ± 153 | 2.0 ± 0.5 | 45.5 | <0.05 |
| Y31 | 2.5 mg/kg, 1-5/2 w | po | 6 | 6 | 19.2 | 21.2 | 159 ± 36 | 259 ± 130 | 1.6 ± 0.6 | 37.1 | <0.05 |
| Y31-1 | 5 mg/kg, 1-5/2 w | po | 6 | 6 | 20.2 | 21.2 | 164 ± 44 | 381 ± 158 | 2.4 ± 1.0 | 55.7 | <0.05 |
| Rapamycin | 5 mg/kg, 1-5/2 w | po | 6 | 6 | 19.8 | 20.3 | 159 ± 32 | 362 ± 100 | 2.4 ± 1.0 | 54.4 | <0.05 |
| Rapamycin | 2.5 mg/kg, 1-5/2 w | po | 6 | 6 | 20.2 | 21.8 | 164 ± 67 | 440 ± 157 | 2.8 ± 0.8 | 63.7 | >0.05 |

Figure 7:
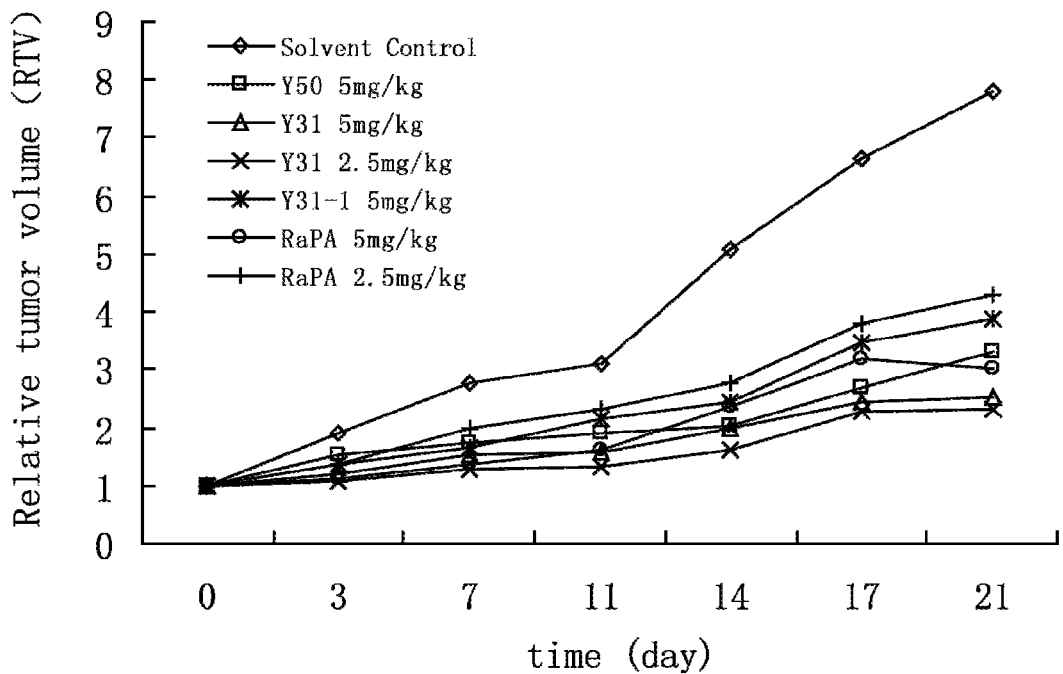
FIG. 7 is a graph illustrating the inhibitory effects of the compounds Y50, Y31, Y31-1 and rapamycin on the growth of human rhabdomyosarcoma Rh30 xenograft on nude mice.

The growth inhibition of Y50, Y31, Y31-1 and rapamycin against human rhabdomyosarcoma RH-30 xenograft on nude Y50 and rapamycin in high dosage (5 mg/kg) group, as shown in table 4 and FIG. 7.

TABLE 5 the experimental therapeutic effects of compounds Y31, CCI-779 and rapamycin against human osteosarcoma U2SO xenograft on nude mice

| Group | Oral Dosage | | Animal Number | | Body Weight (g) | | TV (mm³) | | RTV | T/C (%) | P value |
|---|---|---|---|---|---|---|---|---|---|---|---|
| | | | start | end | start | end | d0 | d21 | | | |
| Solvent Control | 0.4 ml per mouse | 1-5/3 w | 12 | 12 | 19.5 | 18.8 | 87 ± 18 | 2025 ± 514 | 25 ± 11 | | |
| CCI-779 | 2.5 mg/kg | 1-5/3 w | 6 | 6 | 19.9 | 17.7 | 85 ± 17 | 1446 ± 630 | 17 ± 7.0 | 69.0 | >0.05 |
| Rapamycin | 2.5 mg/kg | 1-5/3 w | 6 | 6 | 19.7 | 18.5 | 85 ± 24 | 1230 ± 344 | 15 ± 5.1 | 60.0 | >0.05 |
| Rapamycin | 5 mg/kg | 1-5/3 w | 6 | 6 | 19.5 | 17.5 | 86 ± 20 | 1247 ± 293 | 15 ± 3.4 | 59.0 | >0.05 |
| Y31 | 2.5 mg/kg | 1-5/3 w | 6 | 6 | 18.5 | 20.2 | 90 ± 27 | 975 ± 235 | 12 ± 6.7 | 49.0 | <0.05 |
| Y31 | 5 mg/kg | 1-5/3 w | 6 | 6 | 17.7 | 19.5 | 89 ± 19 | 967 ± 234 | 11 ± 7.2 | 44.0 | <0.05 |

The experimental therapeutic effects of Y31, CCI-779 and rapamycin against human osteosarcoma U2SO xenogragt on nude mice were observed by the same experimental protocol as the above. Results showed that Y31 through oral administration exhibited a significant growth inhibition effect against human osteosarcoma U2SO xenograft on nude mice. CCI-779 and rapamycin in low dosage (2.5 mg/kg) groups exhibited unapparent growth inhibition effects against human osteosarcoma U2SO xenograft on nude mice with T/C values of 69.0% and 60.0% respectively. The compound Y31 in low dosage (2.5 mg/kg) group showed markedly superior growth inhibition against human osteosarcoma U2SO xenograft on nude mice to those of rapamycin and CCI-779.

Example 3

Evaluation on the Distribution Profile of Rapamycin in Nude Mice After the Administration of Y31, Rapamycin and CCI-779

In this experiment, the distribution profile of rapamycin in nude mice was evaluated after Y31, rapamycin and CCI-779 were administrated respectively. After administration in nude mice, the samples of blood plasma, liver and tumor tissues were collected at different times, and the concentrations of the prototype drugs and rapamycin in the blood plasma, liver and tumor tissues were measured by liquid chromatography-mass spectrometry. After the nude mice were administrated with Y31, rapamycin and CCI-779 respectively, the concentrations of the prototype drugs and rapamycin in blood plasma and tissues were listed in tables 6-8, and the major pharmacokinetic parameters were shown in table 9.

TABLE 6

The concentrations of Y31 and rapamycin in blood plasma and tissues after the administration of Y30 to nude mice

| Serial Number of the Animals | Time (h) | Y31 (ng/ml or ng/g) | | | Sirolimus (ng/ml or ng/g) | | |
|---|---|---|---|---|---|---|---|
| | | Blood Plasma | Liver | Tumor | Blood Plasma | Liver | Tumor |
| 1 | 0.5 | 3.03 | 8.61 | BLQ | 215 | 544 | 21.8 |
| 2 | 0.5 | 1.70 | 14.3 | BLQ | 138 | 341 | 25.7 |
| 3 | 0.5 | 2.47 | 6.24 | BLQ | 172 | 233 | 16.3 |
| Mean Value | | 2.40 | 9.72 | | 175 | 373 | 21.3 |
| Standard Deviation | | 0.67 | 4.14 | | 39 | 158 | 4.7 |

TABLE 6-continued

The concentrations of Y31 and rapamycin in blood plasma and tissues after the administration of Y30 to nude mice

| Serial Number of the Animals | Time (h) | Y31 (ng/ml or ng/g) | | | Sirolimus (ng/ml or ng/g) | | |
|---|---|---|---|---|---|---|---|
| | | Blood Plasma | Liver | Tumor | Blood Plasma | Liver | Tumor |
| 4 | 2.0 | 0.70 | 12.4 | BLQ | 131 | 257 | 50.7 |
| 5 | 2.0 | 0.58 | 13.4 | BLQ | 165 | 212 | 60.3 |
| 6 | 2.0 | 0.20 | 17.4 | BLQ | 40.7 | 175 | 42.1 |
| Mean Value | | 0.49 | 14.4 | | 112 | 215 | 51.0 |
| Standard Deviation | | 0.27 | 2.6 | | 64 | 41 | 9.1 |
| 7 | 5.0 | 0.18 | 0.88 | BLQ | 111 | 105 | 84.8 |
| 8 | 5.0 | BLQ | 0.91 | BLQ | 97.1 | 163 | 97.2 |
| 9 | 5.0 | BLQ | 2.16 | BLQ | 74.9 | 163 | 102 |
| Mean Value | | | 1.32 | | 94.3 | 144 | 94.7 |
| Standard Deviation | | | 0.73 | | 18.2 | 33 | 8.9 |
| 10 | 12 | BLQ | BLQ | BLQ | 7.64 | 104 | 60.5 |
| 11 | 12 | BLQ | BLQ | BLQ | 46.1 | 68.2 | 95.8 |
| 12 | 12 | BLQ | BLQ | BLQ | 60.6 | 123 | 74.9 |
| Mean Value | | | | | 38.1 | 98.4 | 77.1 |
| Standard Deviation | | | | | 27.4 | 27.8 | 17.7 |
| 13 | 48 | BLQ | BLQ | BLQ | 3.05 | 29.6 | 34.7 |
| 14 | 48 | BLQ | BLQ | BLQ | 3.73 | 18.9 | 39.7 |
| 15 | 48 | BLQ | BLQ | BLQ | 3.53 | 8.40 | 39.2 |
| Mean Value | | | | | 3.44 | 19.0 | 37.9 |
| Standard Deviation | | | | | 0.35 | 10.6 | 2.8 |

BLQ: below the limit of Quantitation, 0.2 ng/ml (blood plasma); 1.0 ng/g(tissue).

TABLE 7

The concentration of rapamycin in blood plasma and tissues after administration of rapamycin to nude mice

| Serial Number of the Animals | Time (h) | Sirolimus (ng/ml or ng/g) | | |
|---|---|---|---|---|
| | | Blood Plasma | Liver | Tumor |
| 1 | 0.5 | 220 | 507 | 14.6 |
| 2 | 0.5 | 291 | 436 | 33.5 |
| 3 | 0.5 | 62.6 | 477 | 13.7 |
| Mean Value | | 191 | 473 | 20.6 |
| Standard Deviation | | 117 | 36 | 11.2 |
| 4 | 2.0 | 63.3 | 206 | 75.4 |
| 5 | 2.0 | 188 | 139 | 2.96 |
| 6 | 2.0 | 111 | 234 | 73.9 |
| Mean Value | | 121 | 193 | 50.8 |
| Standard Deviation | | 63 | 49 | 41.4 |

TABLE 7-continued

The concentration of rapamycin in blood plasma and tissues after administration of rapamycin to nude mice

| Serial Number of the Animals | Time (h) | Sirolimus (ng/ml or ng/g) | | |
|---|---|---|---|---|
| | | Blood Plasma | Liver | Tumor |
| 7 | 5.0 | 181 | 106 | 31.6 |
| 8 | 5.0 | 45.6 | 213 | 41.0 |
| 9 | 5.0 | 27.6 | 99.0 | 52.5 |
| Mean Value | | 84.7 | 139 | 41.7 |
| Standard Deviation | | 83.9 | 64 | 10.5 |
| 10 | 12 | 17.6 | 71.1 | 42.4 |
| 11 | 12 | 29.3 | 47.3 | 27.9 |
| 12 | 12 | 22.3 | 44.1 | 29.3 |
| Mean Value | | 23.1 | 54.2 | 33.2 |
| Standard Deviation | | 5.9 | 14.8 | 8.0 |
| 13 | 48 | 7.40 | 23.5 | 14.1 |
| 14 | 48 | 0.80 | 10.7 | 15.6 |
| 15 | 48 | 3.92 | 13.1 | 48.1 |
| Mean Value | | 4.04 | 15.8 | 25.9 |
| Standard Deviation | | 3.30 | 6.8 | 19.2 |

TABLE 8

The concentrations of CCI-779 and rapamycin in blood plasma and tissues after administration of CCI-779 to nude mice

| Serial Number of the Animals | Time (h) | CCI-779 (ng/ml or ng/g) | | | Sirolimus (ng/ml or ng/g) | | |
|---|---|---|---|---|---|---|---|
| | | Blood Plasma | Liver | Tumor | Blood Plasma | Liver | Tumor |
| 1 | 0.5 | 39.5 | 549 | 22.1 | 74.4 | 146 | 14.1 |
| 2 | 0.5 | 20.5 | 392 | 4.59 | 138 | 83.0 | 4.39 |
| 3 | 0.5 | 32.6 | 482 | 10.6 | 158 | 197 | 8.59 |
| Mean Value | | 30.9 | 474 | 12.4 | 123 | 142 | 9.03 |
| Standard Deviation | | 9.6 | 79 | 8.9 | 44 | 57 | 4.87 |
| 4 | 2.0 | 6.97 | 103 | 31.1 | 36 | 66.7 | 40.4 |
| 5 | 2.0 | 11.6 | 157 | 28.4 | 185 | 75.6 | 34.2 |
| 6 | 2.0 | 16.4 | 194 | 26.9 | 208 | 153 | 34.4 |
| Mean Value | | 11.7 | 151 | 28.8 | 143 | 98.4 | 36.3 |
| Standard Deviation | | 4.7 | 46 | 2.1 | 93 | 47.5 | 3.5 |
| 7 | 5.0 | 4.18 | 45.5 | 12.5 | 111 | 83.9 | 30.9 |
| 8 | 5.0 | 4.94 | 63.0 | 14.4 | 14.2 | 70.6 | 22.9 |
| 9 | 5.0 | 1.89 | 64.4 | 22.9 | 49.5 | 97.1 | 37.0 |
| Mean Value | | 3.67 | 57.6 | 16.6 | 58.2 | 83.9 | 30.3 |
| Standard Deviation | | 1.59 | 10.5 | 5.5 | 49.0 | 13.3 | 7.1 |
| 10 | 12 | 1.30 | 43.6 | 9.37 | 20.9 | 40.2 | 13.0 |
| 11 | 12 | 1.61 | 18.4 | 12.9 | 4.61 | 27.2 | 23.8 |
| 12 | 12 | 0.90 | 23.7 | 9.31 | 17.2 | 32.2 | 20.6 |
| Mean Value | | 1.27 | 28.6 | 10.5 | 14.2 | 33.2 | 19.1 |
| Standard Deviation | | 0.36 | 13.3 | 2.1 | 8.5 | 6.6 | 5.5 |
| 13 | 48 | 0.16 | 4.97 | 6.48 | 3.07 | 9.79 | 14.0 |
| 14 | 48 | 0.20 | 1.90 | 5.60 | 4.86 | 10.3 | 20.6 |
| 15 | 48 | 0.13 | 2.46 | 7.48 | 1.31 | 7.26 | 15.5 |
| Mean Value | | 0.164 | 3.11 | 6.52 | 3.08 | 9.12 | 16.7 |
| Standard Deviation | | 0.035 | 1.63 | 0.94 | 1.78 | 1.63 | 3.5 |

TABLE 9

The major pharmacokinetic parameters of the substances to be determined in blood plasma and tissues after administration to nude mice

| Administration Mode | Substance to be Determined | Tissue | $T_{max}$ (h) | $C_{max}$ (ng/g or ng/ml) | $AUC_{0-t}$ (ng·h/g or ng·h/ml) | $AUC_{tissue}/AUC_{plasma}$ |
|---|---|---|---|---|---|---|
| Y31 | Sirolimus | Blood Plasma | 0.5 | 175 | 1780 | — |
| | | Liver | 0.5 | 373 | 4031 | 2.26 |
| | | Tumor | 5.0 | 94.7 | 2948 | 1.66 |
| Sirolimus | Sirolimus | Blood Plasma | 0.5 | 191 | 1455 | — |
| | | Liver | 0.5 | 473 | 3053 | 2.10 |
| | | Tumor | 2.0 | 50.8 | 1524 | 1.05 |
| CCI-779 | CCI-779 | Blood Plasma | 0.5 | 30.9 | 106 | — |
| | | Liver | 0.5 | 474 | 1773 | 16.8 |
| | | Tumor | 2.0 | 28.8 | 504 | 4.77 |
| | Sirolimus | Blood Plasma | 2.0 | 143 | 1098 | — |
| | | Liver | 0.5 | 142 | 1661 | 1.51 |
| | | Tumor | 2.0 | 36.3 | 954 | 0.87 |

The nude mice bearing human rhabdomyosarcoma RH-30 xenograft were administered Y31, rapamycin and CCI-779 respectively. The result indicated that, after administration to nude mice, Y31 was rapidly converted to its metabolite rapamycin in vivo, and the prototype drug was low in the blood plasma and tissues with a maximum concentration of less than 20 ng/ml or ng/g, and not detectable 5 hours after the administration. The ratios of rapamycin exposure in blood plasma, liver and tumor tissues after administration of Y31 to those after administration of rapamycin were 1.22, 1.32 and 1.93 respectively.

After administration of CCI-779 to nude mice, both the prototype drug CCI-779 and its metabolite rapamycin could be detected in blood plasma and tissues, and the ratios of the exposures of the metabolite rapamycin and the prototype drug in blood plasma, liver and tumor tissues were 10.4, 0.94 and 1.89 respectively. The ratios of rapamycin exposure in blood plasma, liver and tumor tissues after administration of CCI-779 to those after administration of rapamycin were 0.75, 0.54 and 0.63 respectively.

After administration to nude mice, rapamycin was rapidly absorbed in blood plasma with a peak time of 0.5~2 h, a peak time in liver of 0.5 h which is close to that in blood plasma, and a peak time in tumor of 2~5 h which is late. Rapamycin was eliminated rapidly in blood plasma and liver.

In the three administration groups, the concentrations in blood plasma and liver 48 hours after the administration were 1.96% to 6.42% of the peak concentrations. Rapamycin was eliminated slowly in tumor and the concentration in tumor 48 hours after the administration was 40%~51% of the peak concentration. In the three administration groups, the rapamycin exposures in liver were 2.26, 2.01 and 1.51 times of those in blood plasma respectively, and the rapamycin exposures in tumor were 1.66, 1.05 and 0.87 times of those in blood plasma respectively.

When Y31 was compared with the positive control rapamycin and CCI-779, the exposure of their common effective constituent, rapamycin, in liver were 2.26, 2.01 and 1.51 times of those in blood plasma respectively, and those in tumor were 1.66, 1.05 and 0.87 times of those in blood plasma respectively, which indicated that Y31 had a significant specificity for tumor tissue.

Example 4

Experiments on Immunosuppressive Activity at a Cellular Level

TABLE 10 immunosuppressive activity assay for Y50, Y31, Y230 and rapamycin

| Compound | Cytotoxicity CC50 | T Cells Inhibitory Activity IC50 | Safety Index CC50/IC50 |
| --- | --- | --- | --- |
| Rapamycin | >100 µM (3604 µM) | 4.2 µM | >23.8 |
| Y31 | 93 µM | 0.05 µM | 1860.0 |
| Y50 | >100 µM (7589 µM) | 9.1 µM | >10.9 |
| Y230 | >100 µM (39812 µM) | 5.3 µM | >18.9 |

Results from the immunosuppressive activity assay for compounds Y50, Y31 and Y230 showed that $IC_{50}$ value of the compound Y31 was up to 50 nM, which was significantly superior to those of the parent compound rapamycin and the compound Y50. Meanwhile, the compound Y31 had a fairly high safety index, and the compounds Y50 and Y230 had immunosuppressive activities comparable to that of rapamycin.

Example 5

Systemic Experiments on the Immunosuppressive Activity of Y31

I. The Effect of Rapamycin and Y31 on Proliferation Activity of Mitogen/Allogeneic Antigen-Induced Spleen Lymphocytes in Normal Mice:

Experimental Object:

$^3$H-thymidine incorporation was adopted to measure the effect of the in vitro administered compound on the proliferation function of the spleen lymphocytes of normal mice induced by a mixed culture of mitogen/allogeneic mouse spleen lymphocytes, and evaluate the in vitro immunosuppressive activity of the compound.

3-(4,5-dimethylthylthiazol-2-yl)-2,5-diphenyl tetrazolium bromide (MTT) assay was adopted to measure the effect of the in vitro administered compound on the activity of the spleen lymphocytes of normal mice, and evaluate the cytotoxicity of the compound.

Drugs to be Tested:

Name: rapamycin, Y31; properties, content: white powder

Preparation method: rapamycin and Y31 were stored at 4° C. They were dissolved in DMSO before testing to prepare a stock solution, which was diluted to a desired concentration with the medium when use. The final concentration of DMSO for cell culture was <0.02%, and DMSO at such concentration did not have an influence on cell growth.

Experimental animal: source, gender and strain: BALB/c inbred mice, female, body weight: 18-20 g, purchased from Shanghai laboratory animal center, Chinese Academy of Sciences, whose Certificate of animal breeding is No. SCXK (Shanghai)2002-0010. The animals were raised in a vivarium at SPF level of Shanghai Institute of Materia Medica, Chinese Academy of Sciences, and Certificate for use of the animals is No. SYXK (Shanghai)2003-0029. The animals had been bred for at least one week before use at 22±1° C. of temperature, 55±5% of humidity, and 12 h light-dark cycle. The food and water after sterilized were fed freely by the animals. All the experiments were strictly according to the regulations relating to experimental animals.

Experimental Protocol and Assay:

Measurement of the effects of compounds on the activity of mouse spleen lymphocytes by MTT assay:

100 µl cell suspension of mouse spleen lymphocytes was inoculated on a 96-well plate (4×10$^5$ per well), and the compound at different concentrations was added therein, including additional solvent control or medium background control, wherein, the total volume of each well was 200 µl. After the 96-well plate was placed in an incubator at 37° C. with 5% $CO_2$ for 48 hours, 20 µl (5 mg/ml) of MTT solution was added 6 to 7 hours before the end of incubation. Then after the incubation was completed, 100 µl of supernatant was removed for each well, and 100 µl of MTT solution was added therein. After the 96-well plate was placed in the incubator for 6 to 7 hours, OD values were determined on an ELISA Reader at the wavelength of 570 nm.

Measurement of the effects of compounds on the proliferation function of mouse spleen lymphocytes induced by mitogen by $^3$H-TdR incorporation: 100 µl cell suspension of mouse spleen lymphocytes was inoculated on a 96-well plate (4×10$^5$ per well), followed by addition of 50 µl of ConA (final concentration: 5 µg/ml), 50 µl of LPS (final concentration: 10 m/ml) or 50 µl of compound at different concentrations. The total volume of each well was 200 µl. The test was carried out in triplicate wells for each concentration, and included control wells without ConA/LPS or the compound. After the 96-well plate was placed in an incubator at 37° C. with 5% $CO_2$ for 48 hours, 25 µl of $^3$H-thymidine (10 µCi/ml) was added in each well 8 hours before the end of incubation. The incubation continued until the test was completed, and the cells were harvested by a cell harvester on a glass fiber film, followed by addition of a scintillation fluid. The amount of $^3$H-TdR incorporated in cell DNA was determined by a Beta cell counter (MicroBeta Trilux, PerkinElmer), and the cell proliferation was represented as a cpm value.

Measurement of the Effects of Compounds on the Proliferation Function of Mouse Spleen Lymphocytes Induced by Allogeneic Antigen by $^3$H-TdR Incorporation.

Preparation of Stimulator Cells: a Cell Suspension of Balb/C Mouse Spleen Lymphocytes was irradiated by cesium 137 at 3000 Rads using a Gamma radiometer (Gammacell 3000) to make the cells lose their proliferation ability. After washed by RPMI-1640 for 2 times, the cell concentration was adjusted to $5\times10^6$/ml.

Preparation of responder cells: C57BL/6 mouse spleen lymphocytes were used as the responder cells, and the cell concentration was $5\times10^6$/ml.

Mixed lymphocyte culture: 50 μl cell suspension of C57BL/6 mouse spleen lymphocytes was inoculated on a 96-well plate, and 50 μl cell suspension of BALB/C mouse spleen lymphocytes treated by cesium 137 was added therein, followed by addition of 50 μl compound at different concentrations. The total volume for each well was 200 μl. If the total volume was less than 200 μl, it was supplemented with RMPI-1640 medium. The tests were divided into 3 groups, i.e., BALB/C mouse group, C57BL/6 mouse group and BALB/C and C57BL/6 mice mixed culture group. The test was carried out in triplicate wells for each concentration, and included control wells without the compound, with only the stimulator cells and with only the responder cells. The 96-well plate was incubated in an incubator at 37° C. with 5% $CO_2$ for 3 to 5 days. 8 hours before the end of incubation, 25 μl of $^3$H-thymidine (10 μCi/ml) was added in each well. After the incubation was completed, cells were harvested by a cell harvester on a glass fiber film. After addition of a scintillation fluid, the amount of $^3$H-TdR incorporated in cell DNA was determined by a Beta cell counter (MicroBeta Trilux, PerkinElmer), and the cell proliferation was represented as a cpm value.

Data processing and statistical method: all data were expressed as mean±standard deviation, and all the measuring results on various indexes were processed with Excel 2000 and/or SPSS 11.0 statistical soft packages.

A dosage-response profile was plotted based on the experimental results, and $CC_{50}$ value (50% Cytotoxic concentration) that is the concentration of a compound which causes 50% cells to be killed, and $IC_{50}$ value (50% inhibitory concentration) that is the concentration of a compound that is required for 50% inhibition.

Figure 13:
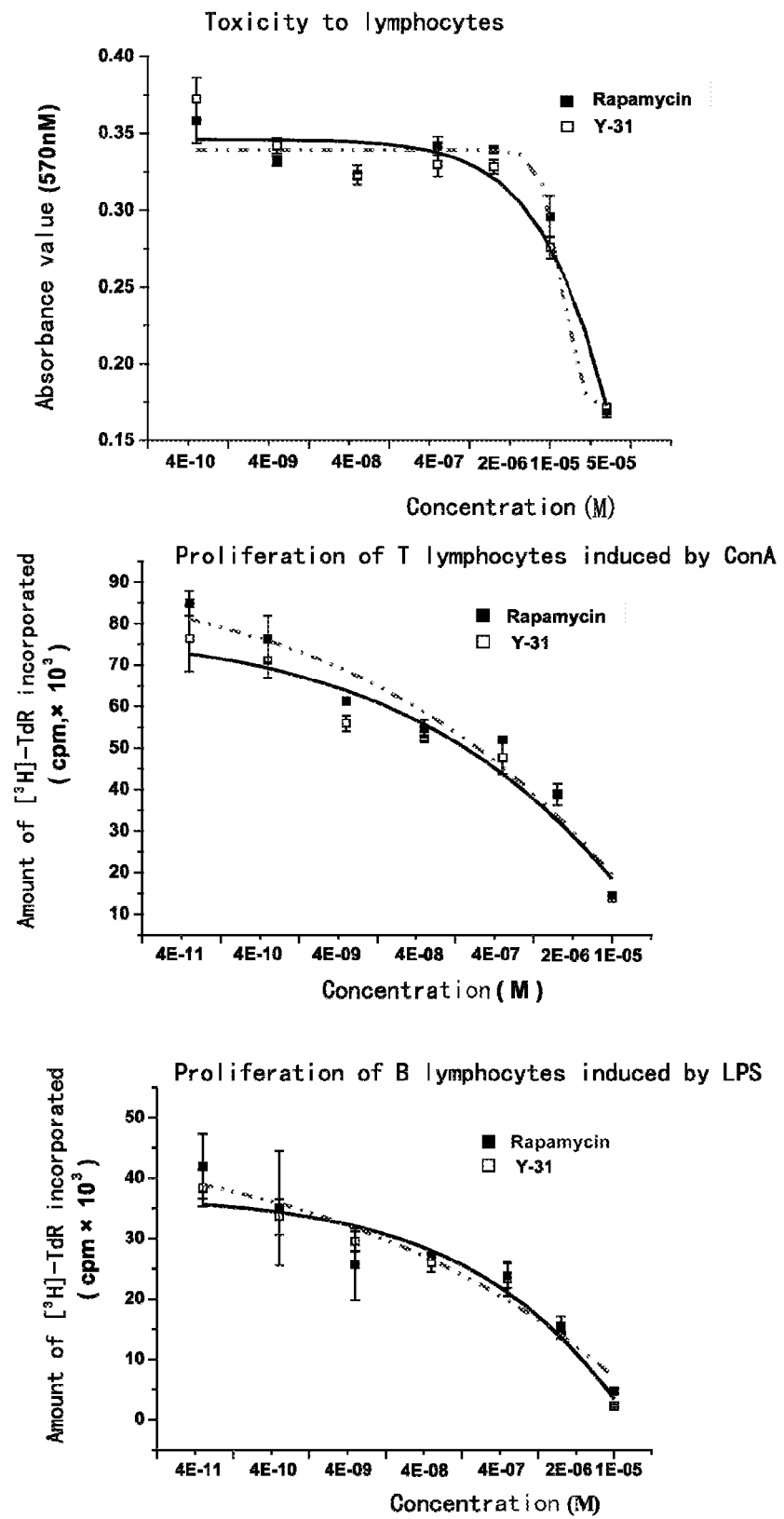
FIG. 13 is a graph illustrating the effects of rapamycin and Y31 on the proliferative activity of the mitogen/allogeneic antigen-induced spleen lymphocytes in normal mice.

Results: the experimental results are as shown in FIG. 13 and table 11.

Rapamycin showed Cytotoxicity of $CC_{50}$=45.51 μM to normal mouse spleen lymphocytes, and concentration-dependently inhibited the proliferation of normal mouse spleen T/B lymphocytes induced by ConA/LPS, and the $IC_{50}$ values thereof were 196.4 nM and 48.8 nM respectively. Y31 exhibited a Cytotoxicity of $CC_{50}$=36.9 μM to normal mouse spleen lymphocytes, and concentration-dependently inhibited the proliferation of normal mouse spleen T/B lymphocytes induced by ConA/LPS, and the $IC_{50}$ values thereof were 330.7 nM and 97.8 nM respectively. Both rapamycin and Y31 exhibited inhibitory activities on the proliferation of allogeneic antigen-induced normal mouse spleen lymphocytes, but the immunosuppressive activity of Y31 was stronger.

TABLE 11

Mixed lymphocyte culture

| Names of samples | Determined concentration (nM) | CPM Mean value | SD | Inhibition |
|---|---|---|---|---|
| BALB/C | — | 28 | 27 | — |
| C57 | — | 516 | 31 | — |
| Control of mixed cultured cells | — | 7354 | 717 | — |
| Rapa | 0.1342 | 4788 | 816 | −35% |
|  | 0.3355 | 3157 | 219 | −57% |
|  | 0.8389 | 1955 | 250 | −73% |
|  | 2.0972 | 1638 | 368 | −78% |
|  | 5.2429 | 1218 | 239 | −83% |
|  | 13.107 | 1250 | 303 | −83% |
|  | 32.768 | 956 | 50 | −87% |
|  | 81.9 | 1012 | 270 | −86% |
|  | 204.8 | 848 | 216 | −88% |
|  | 512 | 1068 | 45 | −85% |
|  | 1280 | 967 | 85 | −87% |
|  | 3200 | 840 | 132 | −89% |
|  | 8000 | 780 | 104 | −89% |
|  | 20000 | 362 | 54 | −95% |
| Y31 | 0.1342 | 1338 | 61 | −82% |
|  | 0.3355 | 1296 | 49 | −82% |
|  | 0.8389 | 1202 | 176 | −84% |
|  | 2.0972 | 1137 | 345 | −85% |
|  | 5.2429 | 1131 | 214 | −85% |
|  | 13.107 | 1137 | 321 | −85% |
|  | 32.768 | 1189 | 325 | −84% |
|  | 81.9 | 1314 | 231 | −82% |
|  | 204.8 | 1090 | 130 | −85% |
|  | 512 | 1436 | 138 | −80% |
|  | 1280 | 1209 | 252 | −84% |
|  | 3200 | 1132 | 72 | −85% |
|  | 8000 | 1190 | 591 | −84% |
|  | 20000 | 815 | 689 | −89% |

The obtained results indicated that rapamycin and its derivatives Y31 could significantly inhibit the proliferation of mitogen/allogeneic antigen-induced lymphocytes, thus having a potent immunosuppressive activity in vitro.

II. The Effects of Rapamycin and Y31 on Delayed Type Hypersensitivity Reaction in Mice Experimental Object:

The delayed type hypersensitivity (DTH) reaction in mice was induced by DNFB to evaluate the inhibition effect of the compound on DTH in vivo. The mice showed ear swelling after the delayed type hypersensitivity reaction was induced in mice, i.e., the mice were sensitized by DNFB and then attacked by DNFB. The effect of a compound on the ear swelling of the mice was observed to evaluate the effect of the compound on the DTH in mice, and thereby studying the effect of the compound on the immune reaction of the body cells.

Drugs to be Tested:

Name: rapamycin and Y31

Properties, content: white powder

Preparation method: the compound was dissolved in anhydrous alcohol to prepare a stock solution (50 mg/ml), which was diluted to the desired concentration when use by using a solution of 5% PEG400, 5% Tween-80 in sterile water as a solvent.

Experimental animals: source, gender and strain: BALB/c inbred mice, female, body weight: 18-20 g, purchased from Shanghai laboratory animal center, Chinese Academy of Sciences, whose Certificate of animal breeding is No. SCXK (Shanghai)2002-0010. The animals were raised at a vivarium at SPF level of Shanghai Institute of Materia Medica, Chinese Academy of Sciences. The Certificate for use of the animals is No. SYXK (Shanghai) 2003-0029. The animals had been bred for at least one week before use at 22±1° C. of temperature, 55±5% of humidity, and 12 h light-dark cycle. The food and water after sterilized were fed freely by the animals. All the experiments were strictly according to the regulations relating to experimental animals.

Experimental Protocol:

2,4-dinitrofluorobenzene (DNFB) is a hapten. DNFB combined with dermal protein to form a complete antigen after sensitizing on feet of mice. One week later, mice were attacked by DNFB on ears to induce a local delayed allergic reaction, i.e., the delayed type hypersensitivity reaction to cause ear swelling, while the delayed type hypersensitivity reaction would not be observed on the ear which had not been attacked. Therefore, the ear swelling can reflect the level of the delayed type hypersensitivity reaction in mice induced by DNFB.

(1) 20 μl of 0.5% DNFB solution in a mixture of acetone and olive oil (4:1) as a solvent was applied on both hind legs of mice for sensitization.

(2) 5 days after the first sensitization, 0.2% DNFB solution was applied on both sides of the right ear of the mice to carry out an immune attack, while a mixture of acetone and olive oil (4:1) was applied on the left ear of the mice as control.

(3) The mice were randomly divided into 4 groups, i.e., model group, Dex group (2 mg/kg/d, oral administration), rapamycin group (1.5 mg/kg/d, intraperitoneal injection) and Y-31 group (1.5 mg/kg/d, intraperitoneal injection).

(4) Thickness of the left and right ears of the mice was measured by a micrometer screw gauge, and the swelling was calculated by subtracting the thickness of the left ear from thickness of the right ear.

Figure 14:
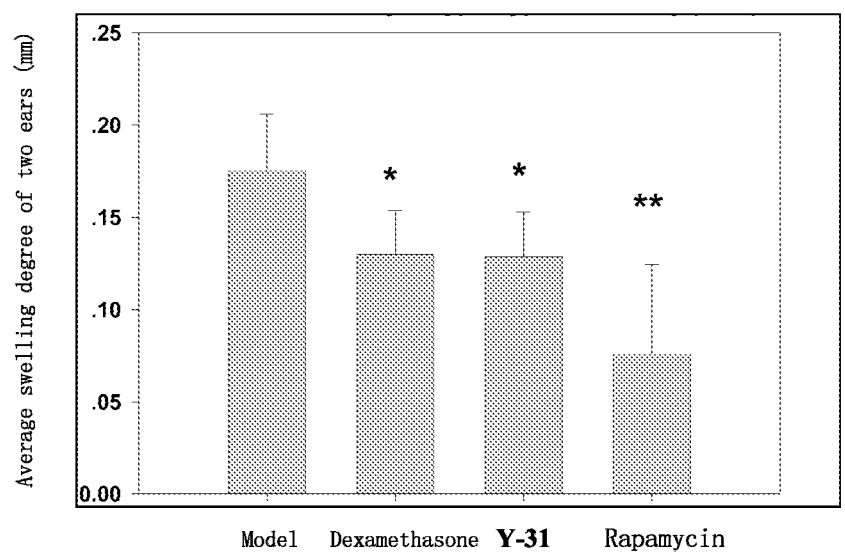
FIG. 14 illustrates the effects of rapamycin and Y31 on the delayed type hypersensitivity reaction in mice.

The experimental results were shown in FIG. 14.

The DTH reaction induced by DNFB is an allergic reaction which is mediated by Th1 cells and involves the activation of T cells and generation of various cytokines. The effect of the compounds on the DTH reaction in BALB/c mice was detected, and the experimental results were shown in FIG. 14. The mice with DNFB-induced delayed type hypersensitivity reaction were taken as the group of model control, and had an average ear swelling degree of 0.175 mm. The mice in the group of positive control (Dex, 2 mg/kg) had an average swelling degree of 0.13 mm, which is significantly different from that of the model control group. The mice in the group of rapamycin had an average ear swelling degree of 0.076 mm, which is significantly different from that of the model control group. The mice in Y31 group had an average ear swelling degree of 0.129 mm, which is significantly different from the model control group.

The experimental results indicated that rapamycin and Y31 could markedly inhibit the DNFB-induced delayed type hypersensitivity in mice.

III. The Effects of Rapamycin and Y31 on the SRBC-Induced Specific Antibody Producing Cells in Mouse Spleen Lymphocytes Experimental Object:

After mice were immunized by sheep red blood cells, there were specific antibody-producing cells in the mouse spleen lymphocytes. The effects of rapamycin and its derivative on the humoral immunity of the mice were observed by detecting the variation of the amount of the specific antibody-producing cells in the mouse spleen lymphocytes after the administration of rapamycin and its derivative.

Drugs to be Tested:

Name: rapamycin and Y31

Properties, content: white powder

Preparation method: the compound was dissolved in anhydrous alcohol to prepare a stock solution (50 mg/ml), which was diluted to the desired concentration when use by using a solution of 5% PEG400, 5% Tween-80 in sterile water as a solvent.

Experimental animals: source, gender and strain: BALB/c inbred mice, female, body weight: 18-20 g, purchased from Shanghai laboratory animal center, Chinese Academy of Sciences, whose Certificate of animal breeding is No. SCXK (Shanghai) 2002-0010. The animals were raised at a vivarium at SPF level of Shanghai Institute of Materia Medica, Chinese Academy of Sciences. The Certificate for use of the animals is No. SYXK (Shanghai) 2003-0029. The animals had been bred for at least one week before use at 22±1° C. of temperature, 55±5% of humidity, and 12 h light-dark cycle. The food and water after sterilized were fed freely by the animals. All the experiments were strictly according to the regulations relating to experimental animals.

Guinea pigs were purchased from Shanghai laboratory animal center, Chinese Academy of Sciences, and serum (complement) thereof was collected for experiment.

Other experimental material: The red blood cells (SRBC) were purchased from Shanghai Jiangnan Biotech Co. Ltd.

Experimental Principle:

It is a classic experimental method to determine the generation of antigen-specific antibody with SRBC hemolytic reaction in SRBC-induced mouse humoral immunity model. The quantitative hemolysis of sheep red blood cells (QHS) assay is an experimental method for evaluating the amount of the antibody secreted, which is based on the principle that the sheep red blood cells are hemolyzed by the anti-SRBC specific antibody secreted by B lymphocytes (plasma cells) to release haemoglobin. After mice are sensitized by sheep red blood cells (SRBC), there will appear cells which can secrete specific antibody in mouse spleen lymphocytes. The Antibody secreted by such cells could hemolyze SRBC with the synergistic action of the complement. Therefore, the amount of the cells secreting the specific antibody can be evaluated by determining the hemolytic degree by spectrophotometry.

Experimental Procedure:

1. BALB/c mice were randomly divided into 5 groups with 6 mice in each group.

Normal control group;

Model control group;

Positive control group: CsA (10 mg/kg);

Rapamycin group (1.5 mg/kg/d, intraperitoneal injection)

Y31 group (1.5 mg/kg/d, intraperitoneal injection)

When immunized, the mice in each group were administered by intraperitoneal injection once daily until 5 days after the immunization. The mice in model control group were administered daily with the solvent.

2. Fresh sheep red blood cells (SRBC) were washed by PBS for 3 times, and diluted to 1:5 (v/v). Each mice was introperitoneally injected with 0.2 ml of the diluted SRBC for sensitizing.

3. QHS assay was carried out 5 days after the sensitization: The mouse spleen was collected to produce the spleen lymphocytes.

Measurement of the hemolytic degree by absorption spectrometry: $5 \times 10^6$ of spleen lymphocytes, 0.2% of SRBC and the serum complement at the optimum dilution ratio were uniformly mixed. The mixture was kept at 37° C. for 1 hour, and then centrifugated at 3000 rpm for 10 min. The supernatant was collected and the OD value was measured at 540 nm to indicate the amount of the cells secreting specific antibody.

Experimental Results (As Shown in Table 12):

The quantitative hemolysis of sheep red blood cells (QHS) assay uses the amount of haemoglobin (OD value) released from the hemolysis of red blood cells by the antibody secreted by B cells to indicate the level of humoral immunity in body.

Inhibition of specific antibody-secreting cells %=(OD of model control group−OD of administration group)/(OD of model control group−OD of normal control group)

TABLE 12

| Group | Animal number | Dosage (mg/kg) | Quantitative hemolysis OD Value | Inhibition of Specific Antibody-secreting cells % |
|---|---|---|---|---|
| Normal Control | 6 | — | 0.3036 | — |
| Model Control | 6 | — | 0.3887 | — |
| CsA | 6 | 10 | 0.3472 | 48.82 |
| Rapamycin | 6 | 1.5 | 0.3012 | 100 |
| Y31 | 6 | 1.5 | 0.3095 | 93.03 |

Conclusion:

Both rapamycin (1.5 mg/kg) and its derivative Y31 (1.5 mg/kg) through intraperitoneal injection could markedly inhibit the amount of the cells secreting anti-SRBC specific antibody in mouse spleen, and their inhibition abilities were superior to that of the positive control CsA. Therefore, rapamycin and Y31 exhibited an significant inhibition against humoral immunity in mice.

IV. Pharmacodynamic Research on the Effects of Rapamycin and Y31 on Acute Graft-Versus-Host Disease (aGVHD) in Mice Experimental Object Donator: BABL/C mice; acceptor: C57B/6 mice. An acute graft-versus-host disease (aGVHD) model was established by implanting bone marrow cells and lymphocytes of BABL/C mice into C57B/6 mice irradiated with fatal dose of γ-ray, and used to evaluate the pharmacodynamic effects of rapamycin and its derivative on mice aGVHD.

Drugs to be Tested:

Name: rapamycin and Y31; properties, content: white powder

Preparation method: the compound was dissolved in anhydrous alcohol to prepare a stock solution (50 mg/ml), which was diluted to the desired concentration by using a solution of 5% PEG400, 5% Tween-80 in sterile water as a solvent when use.

Experimental animals: source, gender and strain: BALB/c inbred mice, female, body weight: 18-20 g, purchased from Shanghai laboratory animal center, Chinese Academy of Sciences, whose Certificate of animal breeding is No. SCXK (Shanghai)2002-0010. The animals were raised at a vivarium at SPF level of Shanghai Institute of Materia Medica, Chinese Academy of Sciences. The Certificate for use of the animals is No. SYXK (Shanghai) 2003-0029. The animals had been bred for at least one week before use at 22±1° C. of temperature, 55±5% of humidity, and 12 h light-dark cycle. The food and water after sterilized were fed freely by the animals. All the experiments were strictly according to the regulations relating to experimental animals.

Experimental Procedure:

1. Total Body Irradiation (TBI):

C57B/6(H-2$^b$) mice, female, 7 weeks old, were used as the acceptor mice to receive 8.5 Gy of total body irradiation in a Gammacell.

2. Bone Marrow Transplantation:

After the acceptor mice received irradiation for 4 to 6 hours, the heterogenetic bone marrow transplantation was carried out.

BABL/C(H-2$^d$) mice, female, 4 weeks old were used as the donator mice. The bone marrow cells in long bone of the mice limbs and the spleen lymphocytes were collected and suspended in a PBS buffer solution respectively by adjusting the cell concentration to 1×10$^8$.

The two kinds of cells were mixed equivalently to prepare a mixed cell suspension. Each acceptor mouse was intravenously injected with 0.5 ml of the suspension.

3. Grouping and Administration

Mice were randomly divided into 3 groups with 10 mice in each group. Mice were administered once daily from the first day when the bone marrow transplantation was carried out.

Model group (solvent control)

Rapamycin group (1.5 mg/kg/d, intraperitoneal injection)

Y-31 group (1.5 mg/kg/d, intraperitoneal injection)

4. Measuring Indexes:

(1) Body weight: weighted once daily;

(2) The survival time of the mice after BMT was recorded.

Experimental Results:

In this experiment, an acute graft-versus-host disease (aGVHD) mouse model was established. After C57B/6 mice received a sub-fatal dose (8.5 Gy) of total body irradiation, they were injected with the bone marrow cells and lymphocytes of BABL/C mice to replicate the aGVHD model. Then, the effects of the compounds on the survival rate and body weight of aGVHD mice were observed.

Figure 15:
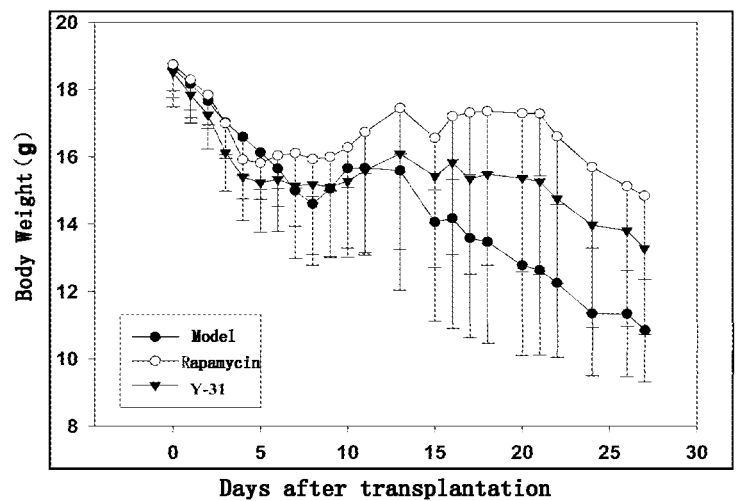
FIG. 15 illustrates the pharmacodynamic research of rapamycin and Y31 on the acute graft-versus-host disease (aGVHD) in mice.
Figure 15:
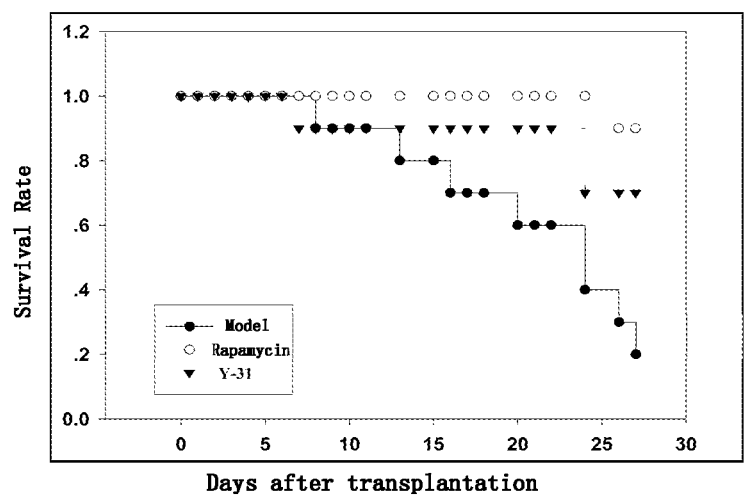

Experimental results were shown in FIG. 15. aGVHD mice markedly lost their weight after the bone marrow transplantation, and some of them were died. Rapamycin and its derivative Y31 could significantly alleviate the weight loss caused by aGVHD induced by heteroplastic transplantation, and markedly increase the survival rate of the aGVHD mice, and therefore exhibited an obvious therapeutic effect.

The experimental results revealed that rapamycin and its derivative Y31 had a good curative effect on the acute graft-versus-host disease (aGVHD) animal model.

V. The Therapeutic Effect of Y31 on Bovine Type II Collagen-Induced Arthritis in DBA/1 Mice Experimental object: DBA/1 mice suffered from arthritis induced by bovine collagen were administrated with Y31, and the therapeutic effect of Y31 on mouse arthritis was evaluated by observing the arthritis index in mice.

Drugs to be Tested:

Name: rapamycin and Y31; properties, content: white powder

Preparation method: the compound was dissolved in anhydrous alcohol to prepare a stock solution (50 mg/ml), which was diluted to the desired concentration when use by using a solution of 5% PEG400, 5% Tween-80 in sterile water as a solvent.

Experimental Animals and Material:

DBA/1 mice, 7 to 8 weeks old, body weight: 20 to 22 g, were provided friendly by Prof. Hiromi Fujiwara from Medical Department of Osaka University, Japan. The animals were raised at a vivarium at SPF level of Shanghai Institute of Materia Medica, Chinese Academy of Sciences. The animals had been bred for at least one week before use at 22±1° C. of temperature, 55±5% of humidity, and 12 h light-dark cycle. The food and water after sterilized were fed freely by the animals. All the experiments were strictly according to the regulations relating to experimental animals.

Freund's complete adjuvant comprising *Mycobacterium tuberculosis* H37Rv strain was purchased from Wako Pure Chemical Industries Ltd. (Osaka, Japan).

Experimental Method:

Arthritis model: bovin type II collagen was added with 0.1 M acetic acid to prepare a solution with a concentration of 20 mg/ml and stored in a refrigerator at 4° C. overnight for dissolution of the collagen. Then the collagen was sufficiently emulsified with equal volume of Freund's complete adjuvant containing *Mycobacterium tuberculosis* H37Rv strain. After anaesthetized, and the male DBA/1 mice were sensitized in their tails with 25 μl per mouse (i.e. 250 μg per mouse). 3 weeks later, the mice were attacked with the same dose. Macroscopic observation on mice limbs was carried out to evaluate the severe dree of arthritis by 4 grade, wherein, 0 represented normal; 1 represented erythema or swelling of one or more phalangeal joints; 2 represented moderate erythema and swelling of below ankle; 3 represented severe erythema and swelling including the knee joint; 4 represented complete erythema and swelling including the knee joint with the joint being deformed, stiff, and disabled. The highest score for each mouse was 16.

Drug treatment: mice were randomly divided into two groups.

Model Control Group

Y31-treating group (1 mg/kg): 14th day after being attacked, the mice started to be administered, and the administration continued for 3 weeks.

Figure 16:
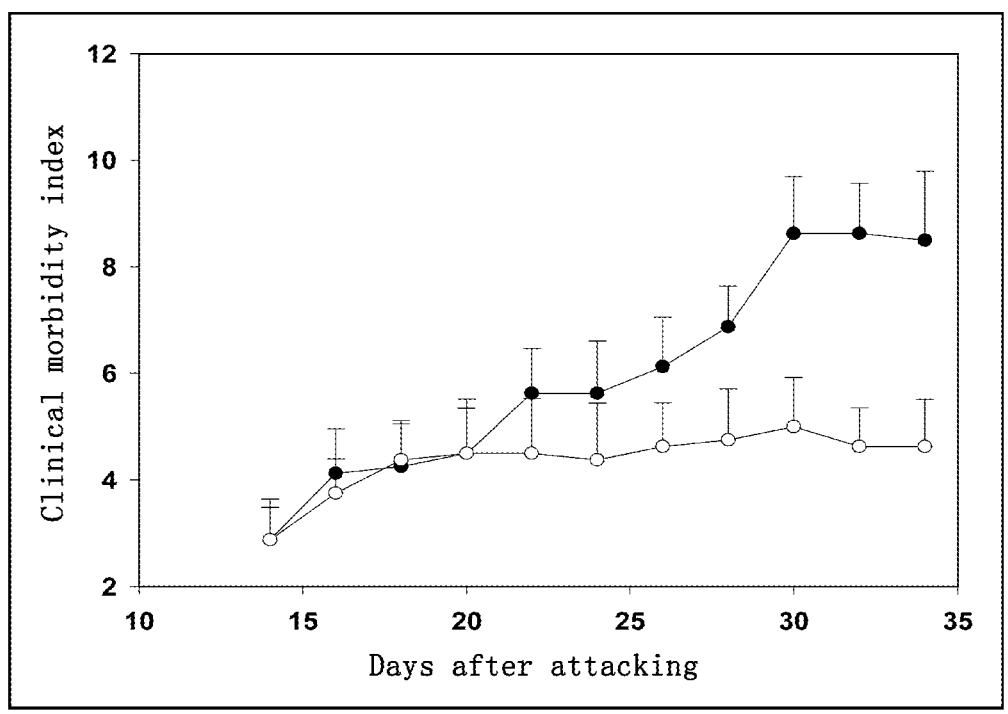
FIG. 16 illustrates the therapeutic effects of Y31 on bovine type II collagen-induced arthritis in DBA/1 mice.

Experimental Results:

Arthritis in DBA/1 mice was induced by subcutaneous injection of bovin type II collage for 2 times. The joint swelling began at the 4$^{th}$ day after attacking One week later, all mice suffered from arthritis, and the swelling of the joints aggravated progressively. At the 14$^{th}$ day, Y31 was applied to the mice. The administration of Y31 could significantly reduce the severe degree of CIA, representing by the markedly alleviated swelling of the mouse limbs was (as shown in FIG. 16, wherein P<0.05), which indicated that Y31 through oral administration could inhibit the development of collagen-induced arthritis in DBA/1 mice.

The invention claimed is:

1. A compound of formula I, or a pharmaceutically acceptable salt thereof:

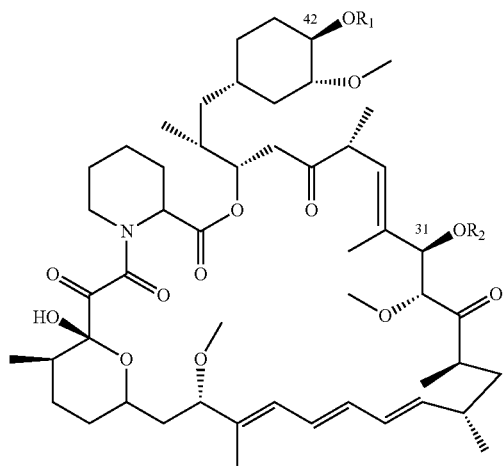

formula I wherein,
$R_1$ is

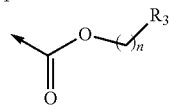

and $R_2$ is H, wherein, n is an integer of 1 to 6, $R_3$ is

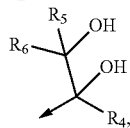

wherein $R_4$, $R_5$ and $R_6$ are each independently H, C1-C6 hydroxyalkyl, C1-C6 alkyl or C2-C6 alkenyl.

2. The compound of formula I or the pharmaceutically acceptable salt thereof according to claim 1, wherein
n is an integer of 1 to 4,
$R_3$ is

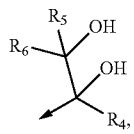

wherein, $R_4$, $R_5$ and $R_6$ are each independently H or C1-C4 hydroxyalkyl.

3. The compound of formula I or the pharmaceutically acceptable salt thereof according to claim 2, wherein
n is an integer of 1 to 2,
$R_3$ is

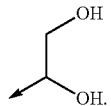

4. The compound of formula I or the pharmaceutically acceptable salt thereof according to claim 3, wherein the compound is:

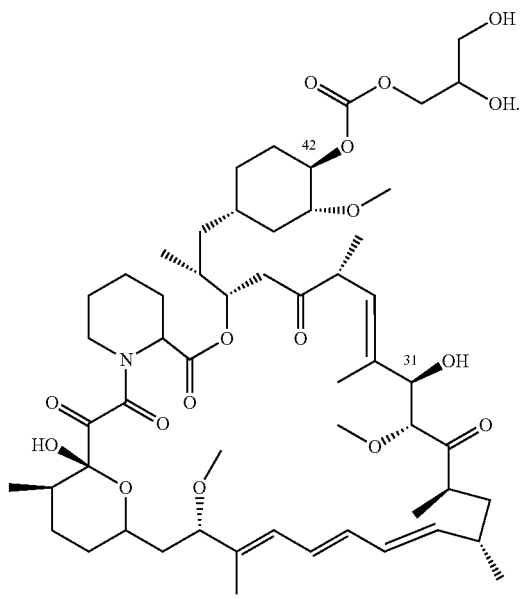

Y31

5. The compound of formula I or the pharmaceutically acceptable salt thereof according to claim 1, wherein the compound or the pharmaceutically acceptable salt thereof may be an optical isomer or a mixture thereof, when $R_3$ comprises a chiral site.

6. A method for preparing the compound of formula I:

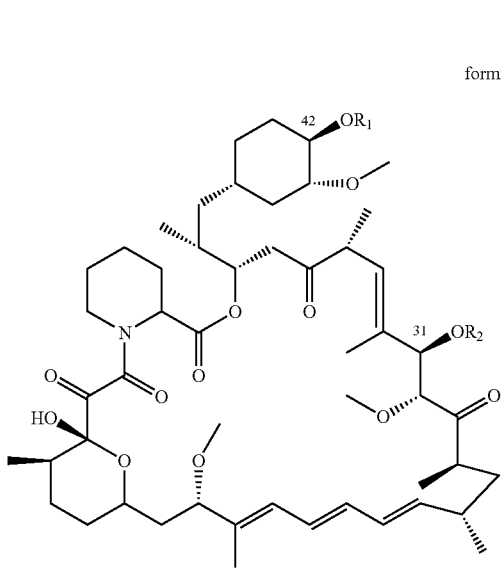

formula I wherein,

R₁ is

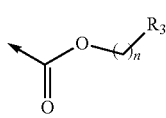

and R₂ is H, wherein, n is an integer of 1 to 6, R₃ is

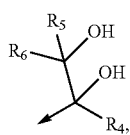

wherein R₄, R₅ and R₆ are each independently H, C1-C6 hydroxyalkyl, C1-C6 alkyl or C2-C6 alkenyl wherein, the compound is prepared according to following process:
in the presence of an proper ratio of imidazole and trimethyl chlorosilane, rapamycin reacts with trimethyl chlorosilane in a solvent selected from the group consisting of dichloromethane, dichloroethane, tetrahydrofuran, acetonitrile and DMF to produce a 31-monoprotected product rapamycin-31-OTMS; after the 42-hydroxyl of Rapamycin-31-OTMS is protected by TBS, the unstable 31-OTMS is deprotected to obtain a 42-monoprotected product rapamycin-42-OTBS, as illustrated in the following scheme:

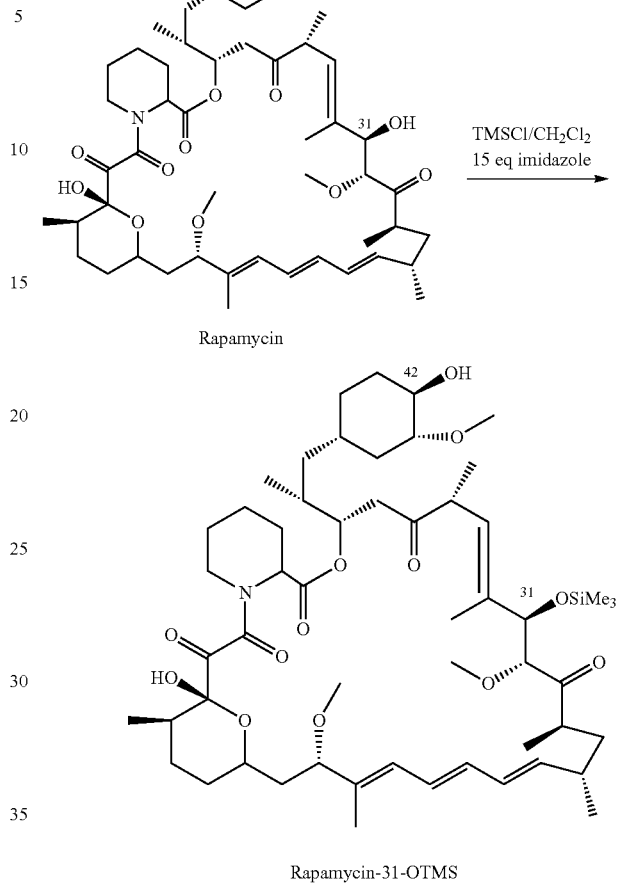

rapamycin-31-OTMS directly reacts with the acyl chloride 3

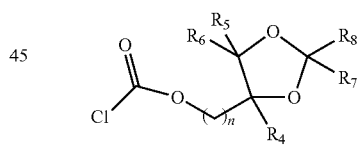

3 to produce a 42-esterified product, which is then depretected the silicon protective group at 31-position to obtain the corresponding 42-monoesterified compound, the resultant compound is further hydrolyzed into a compound wherein R₃ is

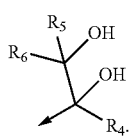

7. A pharmaceutical composition having anti-tumor and anti-cancer activities or immunosuppressive activities, comprising a theraputically effective amount of one or more compound or the pharmaceutically acceptable salt thereof according to claim 1 as an active component, and one or more pharmaceutically acceptable carriers.

8. A method of treating human rhabdomyosarcoma, prostate cancer, breast cancer, renal cancer, adenocarcinoma of lung, cervix cancer, ovarian cancer, epidermoid carcinoma of the oral cavity, malignant mecanona or liver cancer comprising administering to a subject in need thereof an effective amount of the compound of formula I:

formula I

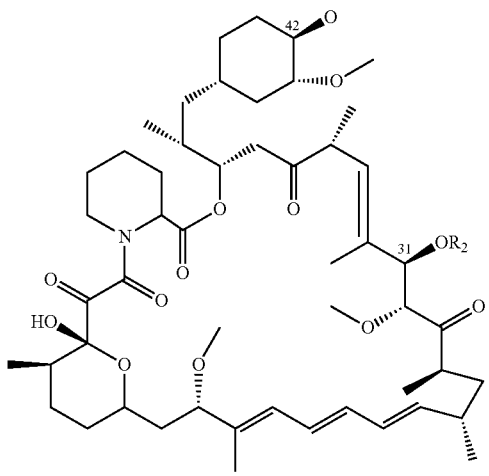

wherein, $R_1$ is

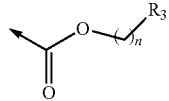

and $R_2$ is H, wherein, n is an integer of 1 to 6, $R_3$ is

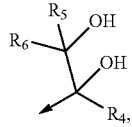

wherein $R_4$, $R_5$ and $R_6$ are each independently H, C1-C6 hydroxyalkyl, C1-C6 alkyl or C2-C6 alkenyl, and $R_7$ and $R_8$ are each independently H or C1-C6 alkyl, or a pharmaceutically acceptable salt thereof.

* * * * *